(12) United States Patent
Hammer et al.

(10) Patent No.: US 8,951,290 B2
(45) Date of Patent: Feb. 10, 2015

(54) MULTI-AXIAL CONNECTION SYSTEM

(75) Inventors: Michael Hammer, Pine Brook, NJ (US); Stephen Termyna, Boonton, NJ (US)

(73) Assignee: Blackstone Medical, Inc., Wayne, NJ (US)

( * ) Notice: Subject to any disclaimer, the term of this patent is extended or adjusted under 35 U.S.C. 154(b) by 1311 days.

(21) Appl. No.: 12/577,503

(22) Filed: Oct. 12, 2009

(65) Prior Publication Data

US 2010/0094349 A1 Apr. 15, 2010

Related U.S. Application Data

(63) Continuation-in-part of application No. 11/388,666, filed on Mar. 24, 2006, now Pat. No. 8,062,339, which is a continuation-in-part of application No. 10/928,955, filed on Aug. 27, 2004, now abandoned.

(60) Provisional application No. 61/105,021, filed on Oct. 13, 2008.

(51) Int. Cl.
*A61B 17/70* (2006.01)
*A61B 17/86* (2006.01)

(52) U.S. Cl.
CPC .......... *A61B 17/7002* (2013.01); *A61B 17/7034* (2013.01); *A61B 17/7035* (2013.01); *A61B 17/7037* (2013.01); *A61B 17/7041* (2013.01); *A61B 17/8605* (2013.01); *A61B 17/7032* (2013.01); *A61B 17/864* (2013.01); *A61B 2017/8655* (2013.01)
USPC ........................................................ 606/267

(58) Field of Classification Search
USPC ......................................... 606/246, 264–278
See application file for complete search history.

(56) References Cited

U.S. PATENT DOCUMENTS

| | | |
|---|---|---|
| 4,946,458 A | 8/1990 | Harms et al. |
| 5,207,678 A | 5/1993 | Harms et al. |
| 5,443,467 A | 8/1995 | Biedermann et al. |
| 5,466,237 A | 11/1995 | Byrd, III et al. |

(Continued)

FOREIGN PATENT DOCUMENTS

| | | |
|---|---|---|
| WO | 98/12976 A1 | 4/1998 |
| WO | 01/22893 A1 | 4/2001 |

(Continued)

OTHER PUBLICATIONS

Written Opinion and International Search Report, International Application No. PCT/US06/10738, dated Aug. 17, 2007.

(Continued)

*Primary Examiner* — Kevin T Truong
*Assistant Examiner* — Michael Araj
(74) *Attorney, Agent, or Firm* — Baker & Hostetler LLP

(57) ABSTRACT

A system and method for a multi-axial connection of an apparatus to bone. The system may include a fastener inserted into a body and a head of the fastener held within a chamber of the body through a combination of a retention ring, a pressure cap, a rod, and a compression element. The compression element applies force to the rod which, in turn, pushed on the pressure cap. The force on the pressure cap urges it against the head of the fastener and pushed it against the retention ring. The force on the retention ring causes it to expand to the walls of the chamber. Once the ring can no longer expand within the chamber, the head of the fastener is wedged between the retention ring and the pressure cap.

12 Claims, 22 Drawing Sheets

(56) References Cited

U.S. PATENT DOCUMENTS

| | | |
|---|---|---|
| 5,474,555 A | 12/1995 | Puno et al. |
| 5,496,321 A | 3/1996 | Puno et al. |
| 5,643,261 A | 7/1997 | Schafer et al. |
| 5,647,873 A | 7/1997 | Errico et al. |
| 5,669,911 A | 9/1997 | Errico et al. |
| 5,690,630 A | 11/1997 | Errico et al. |
| 5,733,286 A | 3/1998 | Errico et al. |
| 5,782,831 A * | 7/1998 | Sherman et al. ............ 606/86 A |
| 5,797,911 A | 8/1998 | Sherman et al. |
| 5,817,094 A | 10/1998 | Errico et al. |
| 5,879,350 A | 3/1999 | Sherman et al. |
| 5,882,350 A | 3/1999 | Ralph et al. |
| 5,885,286 A | 3/1999 | Sherman et al. |
| 5,964,760 A | 10/1999 | Richelsoph |
| 5,997,539 A * | 12/1999 | Errico et al. ................ 606/278 |
| 6,050,997 A | 4/2000 | Mullane |
| 6,063,090 A | 5/2000 | Schlapfer |
| 6,113,601 A | 9/2000 | Tatar |
| 6,187,005 B1 * | 2/2001 | Brace et al. ................ 606/264 |
| 6,248,105 B1 | 6/2001 | Schlapfer et al. |
| 6,280,442 B1 | 8/2001 | Barker et al. |
| RE37,665 E | 4/2002 | Ralph et al. |
| 6,383,190 B1 | 5/2002 | Preissman |
| 6,436,100 B1 | 8/2002 | Berger |
| 6,558,387 B2 | 5/2003 | Errico et al. |
| 6,565,565 B1 | 5/2003 | Yuan et al. |
| 6,582,436 B2 | 6/2003 | Schlapfer et al. |
| 6,613,050 B1 | 9/2003 | Wagner et al. |
| 6,641,586 B2 | 11/2003 | Varieur |
| 6,660,004 B2 | 12/2003 | Barker et al. |
| 6,740,086 B2 | 5/2004 | Richelsoph |
| 6,755,830 B2 | 6/2004 | Minfelde et al. |
| 6,905,500 B2 | 6/2005 | Jeon et al. |
| 6,951,561 B2 | 10/2005 | Warren et al. |
| RE39,089 E | 5/2006 | Ralph et al. |
| 7,081,116 B1 | 7/2006 | Carly |
| 7,087,057 B2 | 8/2006 | Konieczynski et al. |
| 7,163,538 B2 | 1/2007 | Altarac et al. |
| 7,223,268 B2 | 5/2007 | Biedermann |
| 7,306,606 B2 | 12/2007 | Sasing |
| 7,322,981 B2 | 1/2008 | Jackson |
| 7,335,202 B2 | 2/2008 | Matthis et al. |
| 7,338,490 B2 | 3/2008 | Ogilvie et al. |
| 7,678,139 B2 * | 3/2010 | Garamszegi et al. ......... 606/328 |
| 2002/0103487 A1 | 8/2002 | Errico et al. |
| 2003/0004512 A1 | 1/2003 | Farris et al. |
| 2003/0045879 A1 | 3/2003 | Minfelde et al. |
| 2003/0100896 A1 | 5/2003 | Biedermann et al. |
| 2003/0163133 A1 | 8/2003 | Altarac et al. |
| 2003/0167058 A1 | 9/2003 | Shluzas |
| 2003/0216735 A1 | 11/2003 | Altarac et al. |
| 2004/0024464 A1 | 2/2004 | Errico et al. |
| 2004/0102781 A1 | 5/2004 | Jeon |
| 2004/0116929 A1 | 6/2004 | Barker et al. |
| 2004/0127906 A1 | 7/2004 | Culbert et al. |
| 2004/0138662 A1 | 7/2004 | Landry et al. |
| 2004/0153068 A1 | 8/2004 | Janowski et al. |
| 2004/0193160 A1 | 9/2004 | Richelsoph |
| 2004/0243126 A1 | 12/2004 | Carbone et al. |
| 2004/0267264 A1 | 12/2004 | Konieczynski et al. |
| 2005/0033289 A1 | 2/2005 | Warren et al. |
| 2005/0131409 A1 | 6/2005 | Chervitz et al. |
| 2005/0131537 A1 | 6/2005 | Hoy et al. |
| 2005/0131538 A1 | 6/2005 | Chervitz et al. |
| 2005/0131545 A1 | 6/2005 | Chervitz et al. |
| 2005/0203515 A1 | 9/2005 | Doherty et al. |
| 2005/0228392 A1 | 10/2005 | Keyer et al. |
| 2005/0261687 A1 | 11/2005 | Garamszegi et al. |
| 2006/0015105 A1 | 1/2006 | Warren et al. |
| 2006/0025771 A1 | 2/2006 | Jackson |
| 2006/0149241 A1 | 7/2006 | Richelsoph et al. |
| 2006/0161153 A1 | 7/2006 | Hawkes et al. |
| 2006/0241599 A1 | 10/2006 | Konieczynski et al. |
| 2006/0241600 A1 | 10/2006 | Ensign et al. |
| 2007/0055235 A1 | 3/2007 | Janowski et al. |
| 2007/0055241 A1 | 3/2007 | Matthis et al. |
| 2007/0093818 A1 | 4/2007 | Biedermann et al. |
| 2007/0093826 A1 | 4/2007 | Hawkes et al. |
| 2007/0118132 A1 | 5/2007 | Culbert et al. |
| 2007/0123868 A1 | 5/2007 | Culbert et al. |
| 2007/0161996 A1 | 7/2007 | Biedermann et al. |
| 2007/0161999 A1 | 7/2007 | Biedermann et al. |
| 2007/0219556 A1 | 9/2007 | Altarac et al. |
| 2007/0225712 A1 | 9/2007 | Altarac et al. |
| 2007/0225713 A1 | 9/2007 | Altarac et al. |
| 2007/0270813 A1 | 11/2007 | Garamszegi |
| 2008/0015579 A1 | 1/2008 | Whipple |
| 2008/0015580 A1 | 1/2008 | Chao |
| 2008/0015597 A1 | 1/2008 | Whipple |
| 2008/0045953 A1 | 2/2008 | Garamszegi |
| 2008/0097436 A1 | 4/2008 | Culbert et al. |
| 2008/0154315 A1 | 6/2008 | Jackson |
| 2008/0183216 A1 | 7/2008 | Jackson |

FOREIGN PATENT DOCUMENTS

| | | |
|---|---|---|
| WO | 03041601 A1 | 5/2003 |
| WO | 2004/041100 A1 | 5/2004 |
| WO | 2004/071339 A2 | 8/2004 |
| WO | 2008118295 A2 | 10/2008 |

OTHER PUBLICATIONS

International Preliminary Report on Patentability, International Application No. PCT/US06/10738, dated Sep. 25, 2007.

European Search Report and Written Opinion, EP 05 78 9259, dated May 20, 2009.

Definitions of "Integrate" from Dictionary.com, accessed Oct. 20, 2009, 3 pages.

* cited by examiner

MULTI-AXIAL CONNECTION SYSTEM

CROSS-REFERENCE TO RELATED APPLICATIONS

This application claims the benefit of U.S. Provisional Application No. 61/105,021, filed Oct. 13, 2008, entitled "Multi-Axial Connection System," and this application is a continuation-in-part of U.S. application Ser. No. 11/388,666, entitled "Multi-Axial Connection System," filed Mar. 24, 2006 now U.S. Pat. No. 8,062,339, which is a continuation-in-part of U.S. application Ser. No. 10/928,955, entitled "Multi-Axial Connection System," filed Aug. 27, 2004 now abandoned. The aforementioned applications are incorporated herein by reference in their entirety.

FIELD OF THE INVENTION

The invention relates generally a multi-axial connection system for connecting elements in varied moveable and/or fixed positions. Moreover, the invention generally relates to attaching a fastener assembly of the multi-axial connection system to a bone and further to a rod for the purpose of bone fixation.

BACKGROUND OF THE INVENTION

Various systems for connecting fastener elements (e.g., pedicle screws) to elongated supports (e.g., rods) for the purposes of vertebral fixation have been proposed. Examples include the systems described in the following U.S. Patents.

U.S. Pat. No. 5,466,237 relates to a variable locking stabilizer anchor seat and screw. More particularly, this patent relates to a bone interface anchor provided for use with a stabilizer rod for the internal fixation of a spine. The anchor has a seat which accommodates the stabilizer rod and which receives a bone screw for the fixation of the seat to the bone. A compression member cooperates with the seat external to the stabilizer rod and can be tightened to cause a compressive force on the stabilizer rod. The stabilizer rod bears on a rounded surface of the bone screw so as to cause a mating interface between the seat and the bone screw. Subsequently, the position of the seat relative to the bone screw can be locked.

U.S. Pat. No. 5,474,555 relates to a spinal implant system. More particularly, this patent relates to an apparatus for the internal fixation of the spine. The apparatus comprises an assembly having at least two anchors and an elongated stabilizer. The anchors each have means to hold the anchor to the bone, and include receiving means which receive the stabilizer as well as securing means which cooperate with the receiving means by means of the interaction of mating threads to cause the application of compression on the stabilizer into the receiving means.

U.S. Pat. No. 5,669,911 relates to a polyaxial pedicle screw. More particularly, this patent relates to a polyaxial orthopedic device for use with rod implant apparatus. The device includes a screw having a curvate head, a locking collar disposed therearound, and a receiving member having a linearly tapered socket in which the screw and the collar are nested. The locking collar is slotted and tapered, and has a semi-spherical interior volume into which the screw head is initially polyaxially held. The receiving member has a transverse channel formed in it for receiving a rod, and an axial bore having a linearly tapered chamber in the bottom portion thereof. The collar is inserted down the bore from the top to seat in the chamber, and the screw is subsequently inserted up through the bottom of the bore and into the collar. The linear taper of the chamber provides a radially inward force on the locking collar when the collar is forced downward therein. This radially inward force causes the locking collar to crush lock against the head of the screw, therein locking the two at the given angulation. It is the placement of the rod in the transverse channel, against the top of the collar, and the subsequent locking down of the rod in the channel which provides the downward force against the locking collar, which in turn locks the screw in its given angulation.

U.S. Pat. No. 5,879,350 relates to a multi-axial bone screw assembly. More particularly, this patent relates to a multi-axial bone screw assembly including a bone screw having a partially spherical head. The bone screw head is truncated at an upper surface in which a tool receiving recess is defined. The assembly includes a receiver member including a central bore that defines a tapered recess to receive a contracting collet carrying the head of the bone screw. The bore of the receiver member also defines a channel communicating with the recess and configured to receive a spinal rod therein. A portion of the channel is threaded to receive a set screw above the rod. The assembly also includes a contracting collet disposed between the rod and the head of the bone screw. The collet defines a partially spherical recess to receive the head of the bone screw, and includes deflectable fingers that substantially surround the screw head. As the set screw is tightened into the receiver member, the set screw compresses the rod against the collet, which presses the collet into the tapered recess of the receiver member, thereby deflecting the fingers of the collet against the bone screw head.

U.S. Pat. No. 6,063,090 relates to a device for connecting a longitudinal support to a pedicle screw. More particularly, this patent relates to a device used to connect a longitudinal support to a pedicle screw by an accommodating head having a channel to accommodate the longitudinal support, wherein it is possible to freely choose from or mix laterally open, top open or closed accommodating heads. A top open accommodating head facilitates, for example, insertion of the longitudinal support, whereas a lateral opening enables lateral corrections. The pedicle screw and the accommodating head are connected via a conical collet chuck in the accommodating head and by a spherical head on the pedicle screw.

U.S. Pat. No. 6,582,436 relates to a device for connecting a longitudinal support to a bone anchor. More particularly, this patent relates to a device for connecting a longitudinal support to a bone anchor having a rounded head. The device includes a body defining a chamber for receiving the rounded head of the bone anchor and a first channel for receiving the longitudinal support. Further, a first sleeve is slidable over the body for compressing the chamber, a second sleeve is slidable over the body for biasing the longitudinal support against the first sleeve, and a fastener is operatively associated with the body for biasing the second sleeve toward the first sleeve. The forces exerted on the second sleeve by the fastener are transferred to the first sleeve in a plane perpendicular to the central axis. Preferably, the longitudinal support contacts the first sleeve at first and second contact points or zones and one of the sleeves includes at least one extended portion for contacting the other sleeve at least one additional contact point or zone.

U.S. Pat. No. 6,660,004 relates to a multi-axial bone screw assembly. More particularly, this patent relates to a bottom-loading multi-axial bone anchor apparatus. The apparatus includes a receiver member, a crown member, a bone anchor and a retaining member. The receiver member defines an upper opening and a lower opening, which may form part of the same opening, a channel, and a groove. The crown member and bone anchor are loaded into the lower opening of the receiver member, and the retaining member fits around the bone anchor and into the groove in the receiver member. The bone anchor is capable of multi-axial positioning with respect to the receiver member. An elongated member is placed in the channel of the receiver member, contacting the crown member, and a compression member is applied via the upper opening. The compression member presses down on the elongated member, which presses down on the crown member and locks the bone anchor between the crown member and the retaining member.

U.S. Pat. No. 6,740,086 relates to a screw and rod fixation assembly and device. More particularly, this patent relates to a screw and rod fixation assembly for fixing a screw and, optionally, a rod. The screw and rod fixation assembly includes a screw, fixing mechanism, a substantially annular ring, rod seating mechanism, and locking mechanism.

SUMMARY OF THE INVENTION

The foregoing needs are met, to a great extent, by the present invention, wherein in one aspect a system and a method are provided that in some embodiments includes a multi-axial connection system.

In accordance with one embodiment of the present invention, a fixation system is provided, which can comprise a body, wherein the body has a first end and a second end, a body rod receiving channel disposed adjacent the first end of the body, a fastener head receiving chamber disposed adjacent the second end of the body, wherein the fastener head receiving chamber is tapered towards the second end of the body, and wherein the body rod receiving channel and the fastener head receiving chamber are operatively connected, a body engagement element fixably attached to the body, a pressure cap slidably engaged with the body engagement element and disposed within the body, and a compression element configured to cooperate with the body to urge a rod, when the rod is disposed within the body rod receiving channel, into contact with at least part of the pressure cap.

In accordance with another embodiment of the present invention, a method of assembling a fixation system is provided and includes the steps of connecting a pressure cap to a body such that the pressure cap is slideably connected to the body, inserting a fastener having a fastener head into the body such that the head remains within a fastener head receiving chamber of the body, and connecting a compression element to the body.

In accordance with yet another embodiment of the present invention, a fixation system is provided, which can comprise a body, having a first end and a second end being offset from each other, an offset rod receiving channel disposed adjacent the first end of the body, an offset fastener head receiving chamber disposed adjacent the second end of the body, wherein the offset fastener head receiving chamber is tapered, a compression element configured to cooperate with the body to urge the compression element against a rod, when the rod is disposed within the offset rod receiving channel, and an offset compression element configured to cooperate with the body to urge the offset compression element against a head of a fastener, when the head of the fastener is disposed within the offset fastener head receiving chamber.

In accordance with still another embodiment of the present invention, a method of assembling a fixation system is provided and includes the steps of inserting a fastener having a fastener head into an offset body such that the head remains within an offset fastener head receiving chamber of the offset body, connecting a compression element to the body, and connecting an offset compression element to the body.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

For the purposes of describing and claiming the invention, the term "rod" is intended to refer to any elongated structure. Such an elongated structure may be solid or hollow and may have any desired cross-section (e.g., circular, oval, square, rectangular).

Further, for the purposes of describing and claiming the invention, the term "interference fit" is intended to refer to physical contact between two or more components.

The invention allows engagement of the pedicle screw in the accommodating head after the pedicle screw has been inserted into bone. The invention also provides for a fixing mechanism for fixing a screw, wherein the fixing mechanism further includes an inner surface wall having a gripping portion and a non-gripping portion. Further, the present invention provides for a substantially annular ring for guiding and providing mechanical and frictional force to a screw head. Additionally, the present invention provides for a rod seating mechanism operatively engaged to the screw head and including at least one flexible portion capable of being compressed against a portion of a rod therein. Finally, the present invention provides for a locking mechanism for engaging the rod and the rod seating mechanism. The locking mechanism includes a deflecting mechanism for deflecting the at least one flexible portion of the rod seating mechanism against and around the rod as the locking mechanism further engages the at least one flexible portion of the rod seating mechanism.

Figure 1:
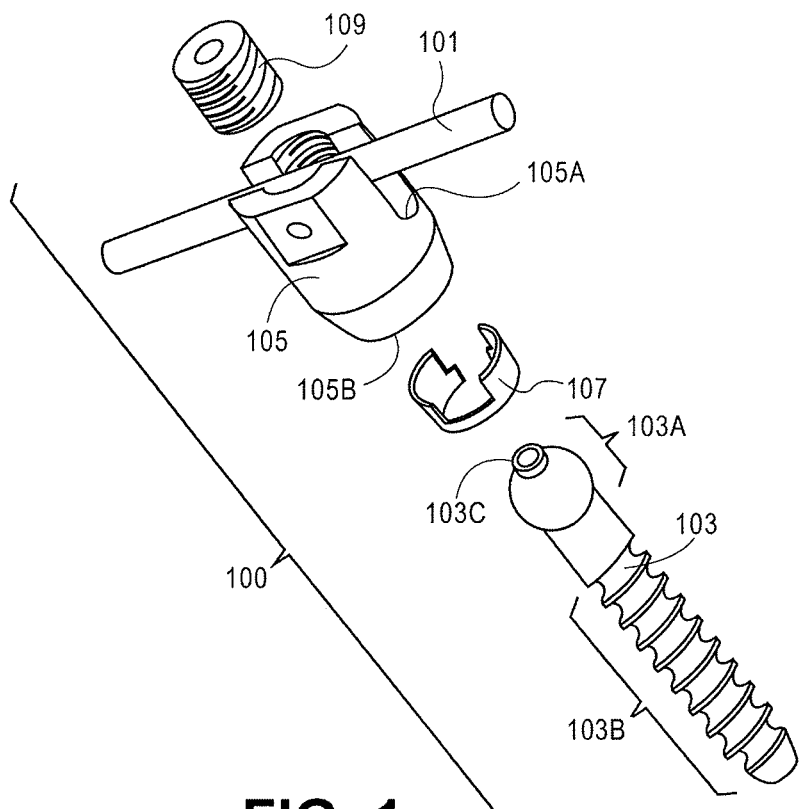
FIG. 1 shows an exploded perspective view of a fastener assembly according to an embodiment of the invention.
Figure 2:
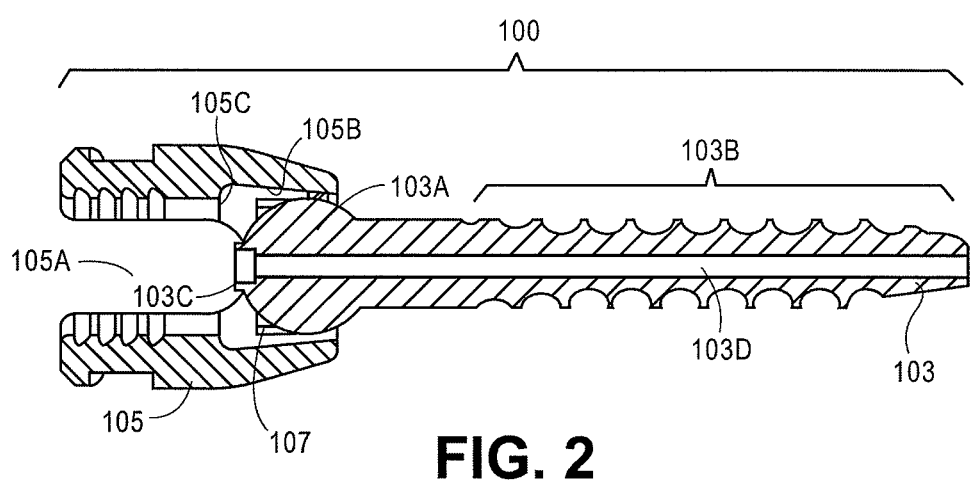
FIG. 2 shows a cross-sectional view of a partially assembled fastener assembly according to the embodiment of FIG. 1 (for clarity, this FIG. does not include the rod or compression member of FIG. 1).

Referring now to FIGS. 1 and 2, a first embodiment of the present invention is shown. As seen in these FIGS., Fastener Assembly 100 may be used in connection with mounting Rod 101 relative to a spine of a patient (of course, one or more such Fastener Assemblies may be used with one or more Rods). More particularly, Fastener Assembly 100 may include Fastener 103 having Head 103A at a first end and Bone Connection Element 103B at a second end (Bone Connection Element 103B may be adapted for attachment on, in and/or to the spine). Further, Head 103A may include at least one Deformation Element 103C thereon.

In one example (which example is intended to be illustrative and not restrictive), at least a portion of Head 103A may be spherical. In another example (which example is intended to be illustrative and not restrictive), Fastener 103 may be a bone screw and Bone Connection Element 103B may comprise threads. In another example (which example is intended to be illustrative and not restrictive), Fastener 103 may be a cannulated bone screw (see Cannulation 103D of FIG. 2). In another example (which example is intended to be illustrative and not restrictive), Deformation Element 103C may substantially surround Cannulation 103D (e.g., where Cannulation 103D exits Head 103A). In another example (which example is intended to be illustrative and not restrictive), Deformation Element 103C may be a substantially circular ring protruding from Head 103A. In another example (which example is intended to be illustrative and not restrictive), Deformation Element 103C (and/or any other portion of Fastener 103 (e.g., Head 103A or the entire Fastener 103)) may include a material which is: (a) softer than a material from which Rod 101 is formed; (b) harder than a material from which Rod 101 is formed; or (c) of essentially the same hardness as a material from which Rod 101 is formed (e.g., the same material from which Rod 101 is formed).

Still referring to FIGS. 1 and 2, it is seen that Fastener Assembly 100 may include Body 105. Body 105 may have a first end and a second end, wherein Rod Receiving Channel 105A for receiving Rod 101 is disposed adjacent the first end of Body 105 and Fastener Head Receiving Chamber 105B is disposed adjacent the second end of Body 105 (as seen in these FIGS., Fastener Head Receiving Chamber 105B may be tapered towards the second end of Body 105 and Rod Receiving Channel 105A and Fastener Head Receiving Chamber 105B may be operatively connected (e.g., a hole in Body 105 may connect Rod Receiving Channel 105A and Fastener Head Receiving Chamber 105B)).

Further, Fastener Assembly 100 may include Retention Ring 107. This Retention Ring 107 may be sized to fit at least partially around Head 103A when Head 103A is disposed within Fastener Head Receiving Chamber 105B. In one example (which example is intended to be illustrative and not restrictive), Retention Ring 107 may be, as shown in the FIGS., of a "split-ring" design.

Further still, Compression Element 109 may cooperate with Body 105 to push Rod 101, when Rod 101 is disposed within Rod Receiving Channel 105A, into contact with at least part of Deformation Element 103C. Such contact between Rod 101 and Deformation Element 103C will deform Deformation Element 103C while pressing Head 103A towards the tapered end (i.e., narrower end) of Fastener Head Receiving Chamber 105B. This action will serve to fix the angular relationship of Fastener 103 relative to Rod 101.

More particularly, the angular relationship of Fastener 103 relative to Rod 101 may be fixed at least in part due to: (a) an interference fit (caused by radial compression) between at least a portion of an outside surface of Head 103A and at least a portion of an inside surface of Retention Ring 107; (b) an interference fit (caused by radial compression) between at least a portion of an outside surface of Retention Ring 107 and at least a portion of an inside surface of Fastener Head Receiving Chamber 105B; and/or (c) an interference fit between at least a portion of an outside surface of Rod 101 and Deformation Element 103C.

In one example (which example is intended to be illustrative and not restrictive), Compression Element 109 may have threads which cooperate with complementary threads of Body 105. In another example (which example is intended to be illustrative and not restrictive), Compression Element 109 may have external threads which cooperate with complementary internal threads of Body 105 (e.g., Compression Element 109 may be a set screw). In another example (which example is intended to be illustrative and not restrictive), Compression Element 109 may have internal threads which cooperate with complementary external threads of Body 105 (e.g., Compression Element 109 may be a nut). In another example (which example is intended to be illustrative and not restrictive), Compression Element 109 may have one or more indentations, protrusions and/or drive faces for receiving torque from a drive tool (e.g., the female hex).

Reference will now be made to the elements shown in FIGS. 1 and 2 in connection with the description of an example installation procedure. Such an example installation procedure is applicable to this embodiment of the fastener assembly of the present invention and, of course, is intended to be illustrative and not restrictive.

More particularly, a guide wire may first be attached to a pedicle of the spine. The free end of the guide wire may then be passed through Fastener 103 (via Cannulation 103D). Fastener 103 (e.g., a pedicle screw) may then be inserted (e.g., screwed) into the pedicle of the spine. Of note, such a pedicle screw may be self-tapping into a hole bored into the pedicle or the hole bored into the pedicle may be pre-tapped. Of further note, such a pedicle screw may be driven into bone with any desired tool (e.g., a hand or power driver applying torque through Rod Receiving Channel 105A and Fastener Head Receiving Chamber 105B).

In one example (which example is intended to be illustrative and not restrictive), such a pedicle screw may be driven into bone with a torque applying tool that engages one or more indentations, protrusions and/or drive faces on Head 103A (e.g., the four scallops).

In one example (which example is intended to be illustrative and not restrictive), Fastener 103 may be driven into bone by itself. Next, a body/retention ring assembly (e.g., including Body 105 having Retention Ring 107 already disposed within Fastener Head Receiving Chamber 105B) may be placed (or "snapped") onto Fastener 103.

In this regard, as Body 105 is subsequently pushed onto Head 103A, Retention Ring 107 is pushed against the Back Wall 105C (FIG. 2) of Fastener Head Receiving Chamber 105B and Retention Ring 107 is free to expand outward enabling Head 103A to pass through. Once Head 103A pushes through the bottom of Retention Ring 107, Head 103A remains captured (since Retention Ring 107 would have no room to expand as it was pulled forward by Head 103A towards the tapered (i.e., narrowed) end of Fastener Head Receiving Chamber 105B).

Next, Rod 101 may be placed in Rod Receiving Channel 105A (with Rod 101 coming into contact with Deformation Element 103C).

Finally, as Compression Element 109 (e.g., a set screw) is threaded into Body 105, Compression Element 109 clamps the components in a set position (that is, Compression Element 109 pushes Rod 101 against Deformation Element 103C (and, depending upon the size and shape of Rod 101, Deformation Element 103C and Head 103A, against a portion of Head 103A)). Of note, during this clamping process Deformation Element 103C is deformed (e.g., to form a surface complementary to the portion of Rod 101 causing the deformation) and the result is improved locking (e.g., of the angular relationship between Rod 101 and Fastener 103). Of further note, it is believed that Deformation Element 103C is particularly useful in enabling secure locking of cannulated fasteners, such as cannulated pedicle screws (it is believed that a cannulation (without the use of a deformation element according to the present invention) may tend to compromise the ability to lock the multi-axial adjustability against the rod (e.g., due to a circular cross-section of the rod)).

In another example (which example is intended to be illustrative and not restrictive), rather than driving Fastener 103 into bone by itself and then placing a body/retention ring assembly thereon, Fastener 103 may be captured within body/retention ring assembly as discussed above and then the entire body/retention ring/fastener assembly may be attached to the bone (e.g., by using a driving tool such as a hand or power driver to drive the pedicle screw through the hole provided in Body 105 between Rod Receiving Channel 105A and Fastener Head Receiving Chamber 105B).

Figure 3:
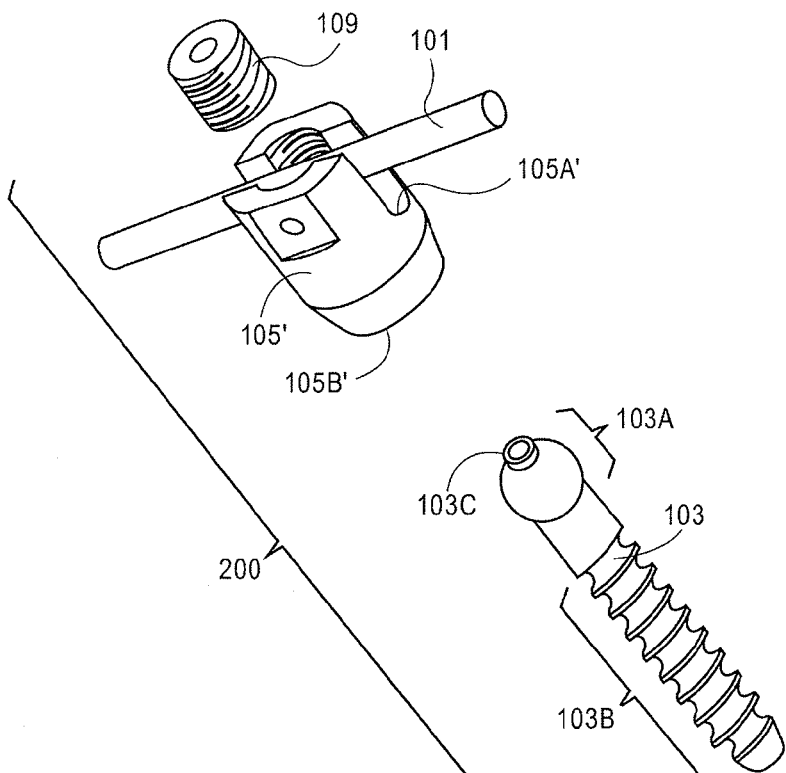
FIG. 3 shows an exploded perspective view of a fastener assembly according to another embodiment of the invention.
Figure 4:
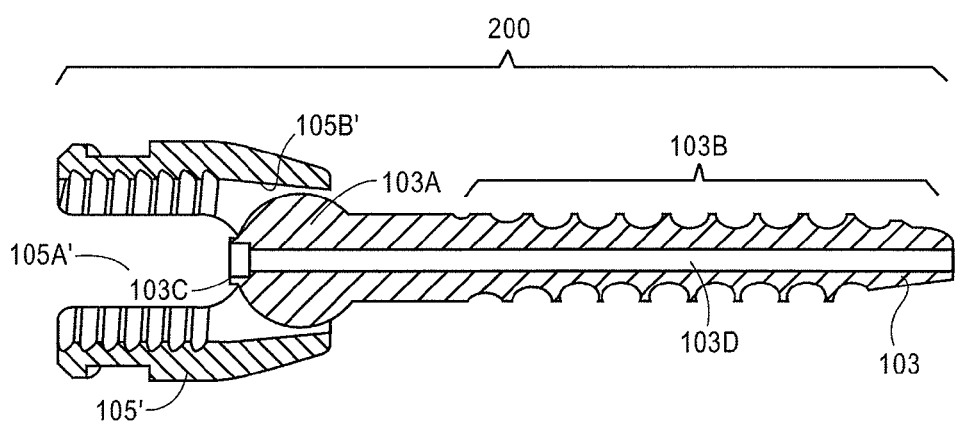
FIG. 4 shows a cross-sectional view of a partially assembled fastener assembly according to the embodiment of FIG. 3 (for clarity, this FIG. does not include the rod or compression member of FIG. 3).

Referring now to FIGS. 3 and 4, another embodiment of the present invention is shown. This embodiment is similar to the embodiment shown in FIGS. 1 and 2 and, in this regard, the same elements will be identified by the same reference numerals (such similar elements will not be described again in detail). Of note, the main difference between the embodiment of these FIGS. 3 and 4 and the embodiment of FIGS. 1 and 2 is that in this embodiment Fastener Assembly 200 does not utilize Retention Ring 107.

More particularly, Fastener Assembly 200 may again be used in connection with mounting Rod 101 relative to a spine of a patient (of course, one or more such Fastener Assemblies may be used with one or more Rods). Further, Fastener Assembly 200 may include Fastener 103 (having Head 103A, Bone Connection Element 103B and at least one Deformation Element 103C).

Still referring to FIGS. 3 and 4, it is seen that Fastener Assembly 200 may further include Body 105' (Body 105' may have a first end and a second end, wherein Rod Receiving Channel 105A' for receiving Rod 101 is disposed adjacent the first end of Body 105' and Fastener Head Receiving Chamber 105B' is disposed adjacent the second end of Body 105'). As seen in these FIGS., Fastener Head Receiving Chamber 105B' may be tapered towards the second end of Body 105' and a hole may be disposed through Body 105' to connect Rod Receiving Channel 105A' and Fastener Head Receiving Chamber 105B'.

Of note, the tapered (i.e., narrow) end of Fastener Head Receiving Chamber 105B' may be made sufficiently small so as to prohibit Head 103A from passing therethrough (while Rod Receiving Channel 105A' and the hole in Body 105' connecting Rod Receiving Channel 105A' to Fastener Head Receiving Chamber 105B' may be made sufficiently large so as to allow Head 103A to pass therethrough).

In this regard, Fastener Assembly 200 may be installed by inserting Fastener 103 through Body 105' such that Head 103A comes to rest in Fastener Head Receiving Chamber 105B' (see FIG. 4). Fastener 103 may then be inserted (e.g., into the pedicle of the spine) as discussed above (e.g., a guide wire may be used to guide Fastener 103 and either a self-tapping bone screw may be driven into a hole in the bone or a pre-tapped hole in the bone may be provided).

Finally, Compression Element 109 may cooperate with Body 105' to push Rod 101, when Rod 101 is disposed within Rod Receiving Channel 105A', into contact with at least part of Deformation Element 103C to deform Deformation Element 103C while pressing Head 103A towards the tapered end (i.e., narrower end) of Fastener Head Receiving Chamber 105B. This action will fix the angular relationship of Fastener 103 relative to Rod 101 (the angular relationship of Fastener 103 relative to Rod 101 may be fixed at least in part due to: (a) an interference fit (caused by radial compression) between at least a portion of an outside surface of Head 103A and at least a portion of an inside surface of Fastener Head Receiving Chamber 105B'; and/or (b) an interference fit between at least a portion of an outside surface of Rod 101 and Deformation Element 103C.

Figure 5:
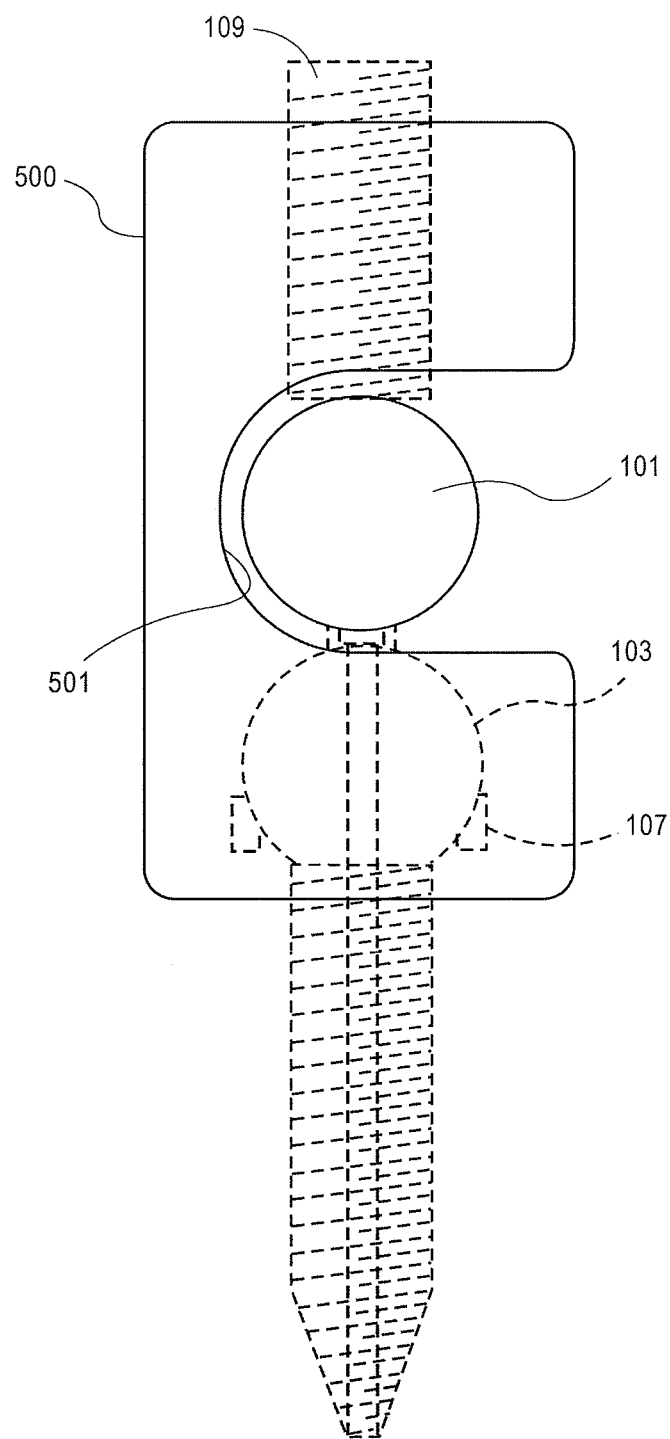
FIG. 5 shows a side view of a fastener assembly according to another embodiment of the invention.
Figure 6:
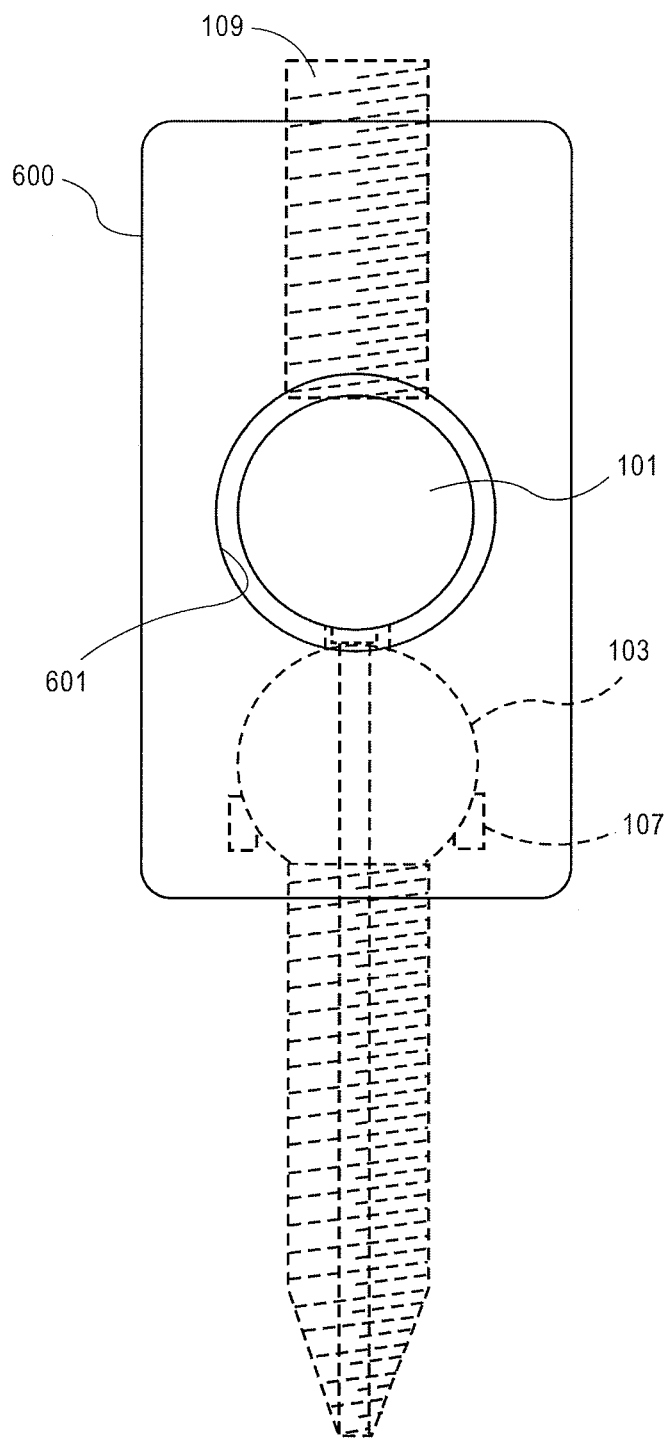
FIG. 6 shows a side view of a fastener assembly according to another embodiment of the invention.

Referring now to FIGS. 5 and 6, two other embodiments of a fastener assembly body are shown. In this regard, it is noted that Body 105 of FIGS. 1 and 2 has an upward facing Rod Receiving Channel 105A for receiving Rod 101. Likewise, Body 105' of FIGS. 3 and 4 has an upward facing Rod Receiving Channel 105A' for receiving Rod 101. In contrast, it is seen in FIG. 5 that Body 500 includes a sideward facing Rod Receiving Channel 501 for receiving Rod 101 (Fastener 103, Compression Element 109 and Retention Ring 107 are shown in phantom and are essentially the same elements as described in detail above). Further, it is seen in FIG. 6 that Body 600 includes a "tunnel-type" Rod Receiving Channel 601 for receiving Rod 101 (Fastener 103, Compression Element 109 and Retention Ring 107 are shown in phantom and are essentially the same elements as described in detail above). Of note, the embodiments of these FIGS. 5 and 6 may operate as discussed above (e.g., the body may include a tapered chamber for facilitating an interference fit between the components disposed therein).

Figure 7:
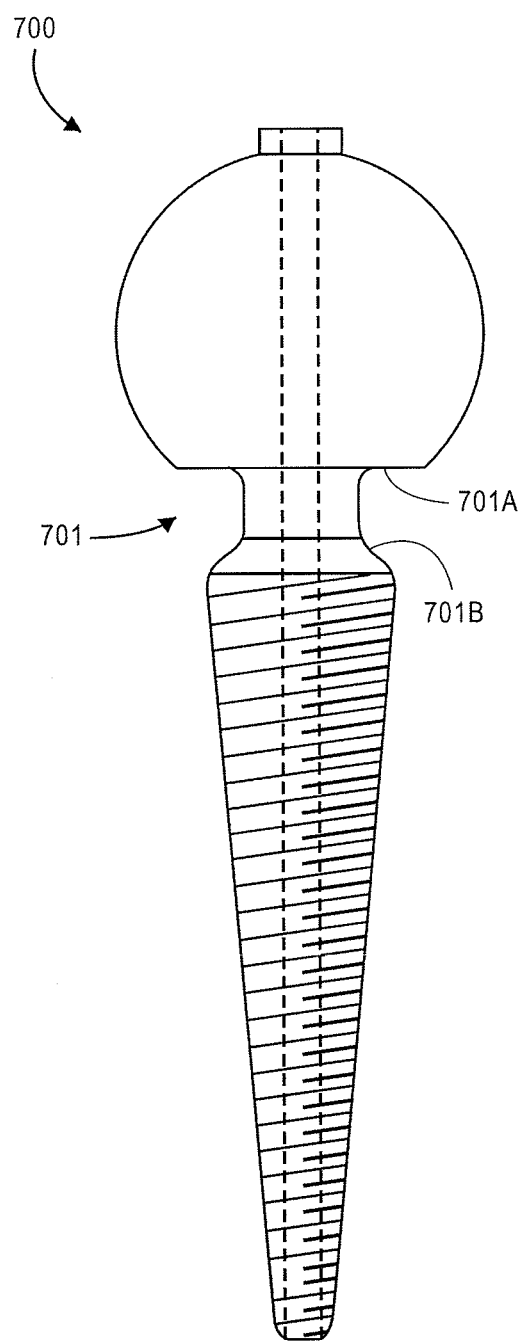
FIG. 7 shows a side view of a fastener according to an embodiment of the invention.

Referring now to FIG. 7, another embodiment of a fastener for use with the invention is shown. Of note, Fastener 700 is depicted here as a bone screw, although other types of bone attaching mechanisms may, of course, be utilized (e.g., a shaft having a hook on the end). In any case, it is seen that in this embodiment Undercut 701 is provided (Undercut 701 may be formed, for example, by a flattening of the Bottom of the Head 701A of the bone screw and/or by a narrowing of a portion of the Shaft 701B of the bone screw. By using such Undercut 701, Fastener 700 may provide increased clearance in the area where Fastener 700 extends from the body of the fastener assembly (wherein such increased clearance may translate into an increase in a maximum angle that Fastener 700 may obtain in relation to the fastener body and/or the rod.

Figure 8A:
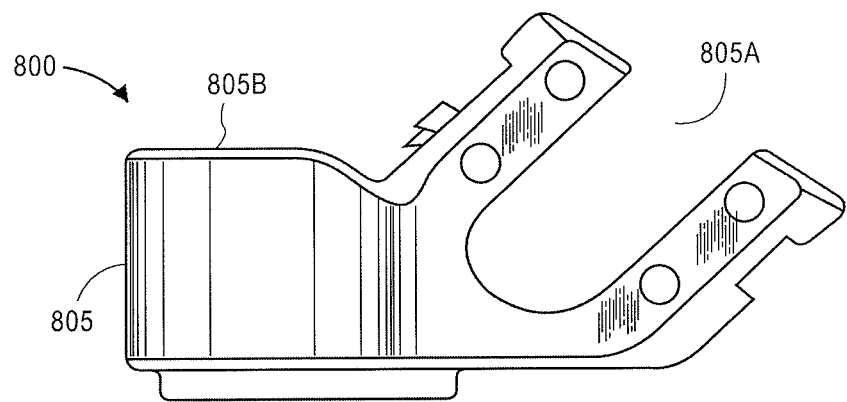
FIGS. 8A and 8B show, respectively, an elevational view and a perspective view of an offset design according to an embodiment of the invention.
Figure 8B:
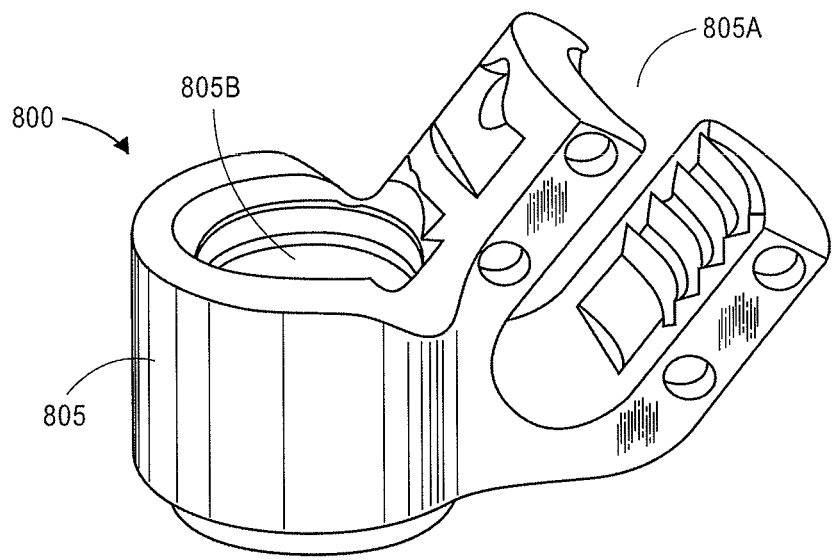

Referring now to FIGS. 8A and 8B, it is seen that these FIGS. show, respectively an elevational view and a perspective view of an offset design according to an embodiment of the invention. In the example of these FIGS. 8A and 8B (which example is intended to be illustrative and not restrictive), Body 805 includes a lateral offset (e.g., an 8 mm lateral offset) between Fastener Head Receiving Chamber 805B and Rod Receiving Channel 805A. Further, Rod Receiving Channel 805A is angled (e.g., 50 degrees) from vertical (and from a vertical axis disposed through Fastener Head Receiving Chamber 805B). Of note, such offset design may be used in a manner similar to that described with respect to the non-offset designs (e.g., Body 105) disclosed herein (for example, a first compression element, such as a set screw (not shown in these FIGS. 8A and 8B), may be used to fix the rod (not shown in these FIGS. 8A and 8B) relative to the body and a second compression element, such as a set screw (not shown in these FIGS. 8A and 8B), may be used to fix the bone screw (not shown in these FIGS. 8A and 8B) relative to the body).

Figure 9A:
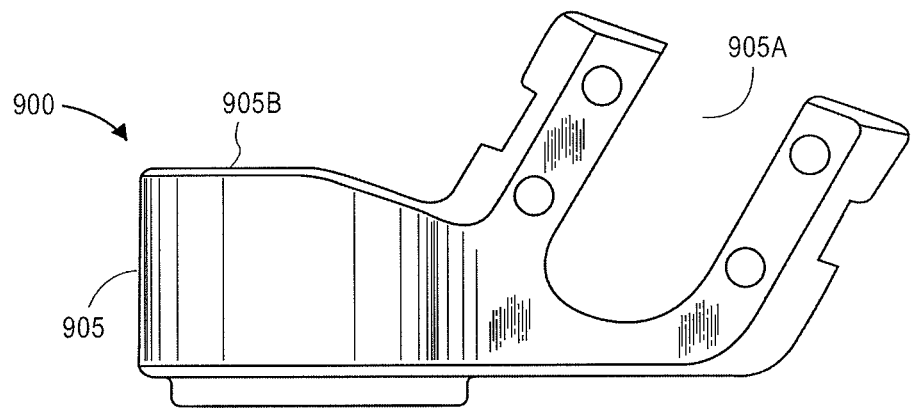
FIGS. 9A and 9B show, respectively, an elevational view and a perspective view of an offset design according to an embodiment of the invention.
Figure 9B:
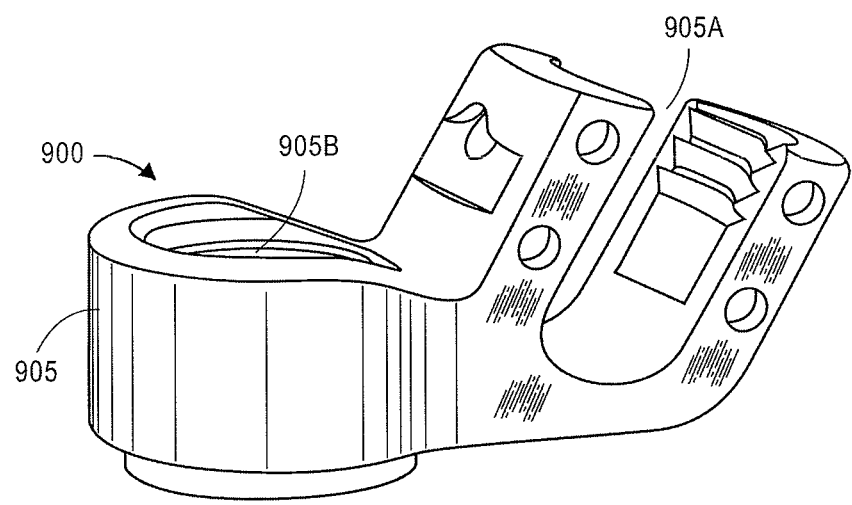

Referring now to FIGS. 9A and 9B, it is seen that these FIGS. show, respectively an elevational view and a perspective view of an offset design according to an embodiment of the invention. In the example of these FIGS. 9A and 9B (which example is intended to be illustrative and not restrictive), Body 905 includes a lateral offset (e.g., an 11 mm lateral offset) between Fastener Head Receiving Chamber 905B and Rod Receiving Channel 905A. Further, Rod Receiving Channel 905A is angled (e.g., 25 degrees) from vertical (and from a vertical axis disposed through Fastener Head Receiving Chamber 905B). Of note, such offset design may be used in a manner similar to that described with respect to the non-offset designs (e.g., Body 105) disclosed herein (for example, a first compression element, such as a set screw (not shown in these FIGS. 9A and 9B), may be used to fix the rod (not shown in these FIGS. 9A and 9B) relative to the body and a second compression element, such as a set screw (not shown in these FIGS. 9A and 9B), may be used to fix the bone screw (not shown in these FIGS. 9A and 9B) relative to the body).

Figure 10A:
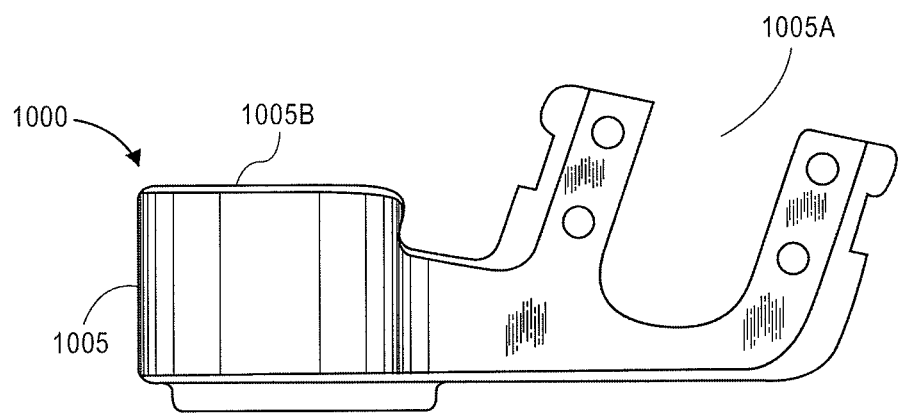
FIGS. 10A and 10B show, respectively, an elevational view and a perspective view of an offset design according to an embodiment of the invention.
Figure 10B:
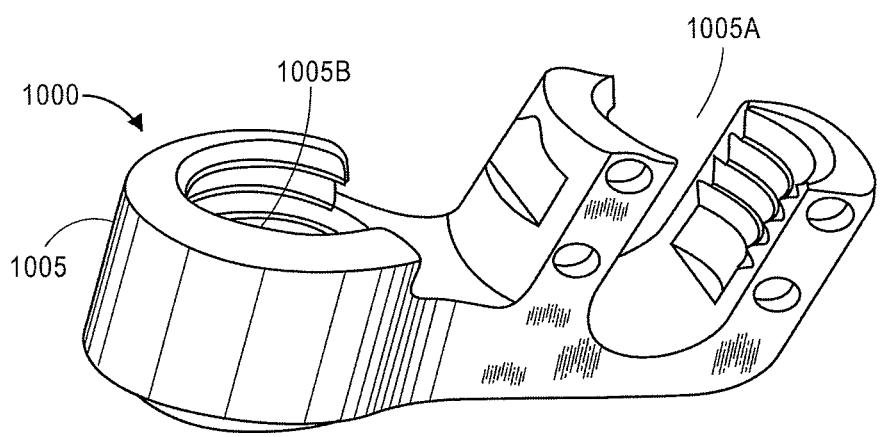

Referring now to FIGS. 10A and 10B, it is seen that these FIGS. show, respectively an elevational view and a perspective view of an offset design according to an embodiment of the invention. In the example of these FIGS. 10A and 10B (which example is intended to be illustrative and not restrictive), Body 1005 includes a lateral offset (e.g., a 14 mm lateral offset) between Fastener Head Receiving Chamber 1005B and Rod Receiving Channel 1005A. Further, Rod Receiving Channel 1005A is angled (e.g., 15 degrees) from vertical (and from a vertical axis disposed through Fastener Head Receiving Chamber 1005B). Of note, such offset design may be used in a manner similar to that described with respect to the non-offset designs (e.g., Body 105) disclosed herein (for example, a first compression element, such as a set screw (not shown in these FIGS. 10A and 10B), may be used to fix the rod (not shown in these FIGS. 10A and 10B) relative to the body and a second compression element, such as a set screw (not shown in these FIGS. 10A and 10B), may be used to fix the bone screw (not shown in these FIGS. 10A and 10B) relative to the body).

Of note, the offset designs may or may not utilize a screw with a deformation element. For example, a screw with a deformation element may be utilized such that the compression element interfacing with the screw presses down on and deforms the deformation element. In another example, a screw with a deformation element may be utilized such that the compression element interfacing with the screw presses down on the screw head itself but the compression element includes a cavity adjacent the screw head and aligned with the deformation element such that the deformation element does not deform. In another example, the screw head may not have a deformation element at all.

Of further note, the offset designs may ease assembly of the fixation system (e.g., by providing a surgeon laterally offset/ angled options when connecting the spinal rod(s)).

In another embodiment (applicable to both the offset and non-offset designs), the body may (before being fixed relative to the bone screw): (a) be circumferentially rotatable on the head of the bone screw around the longitudinal axis of the bone screw; and/or (b) have a desired degree of angular freedom (e.g., 26 degrees from the longitudinal axis of the bone screw (or 52 degrees from one side to the other).

Figure 11:
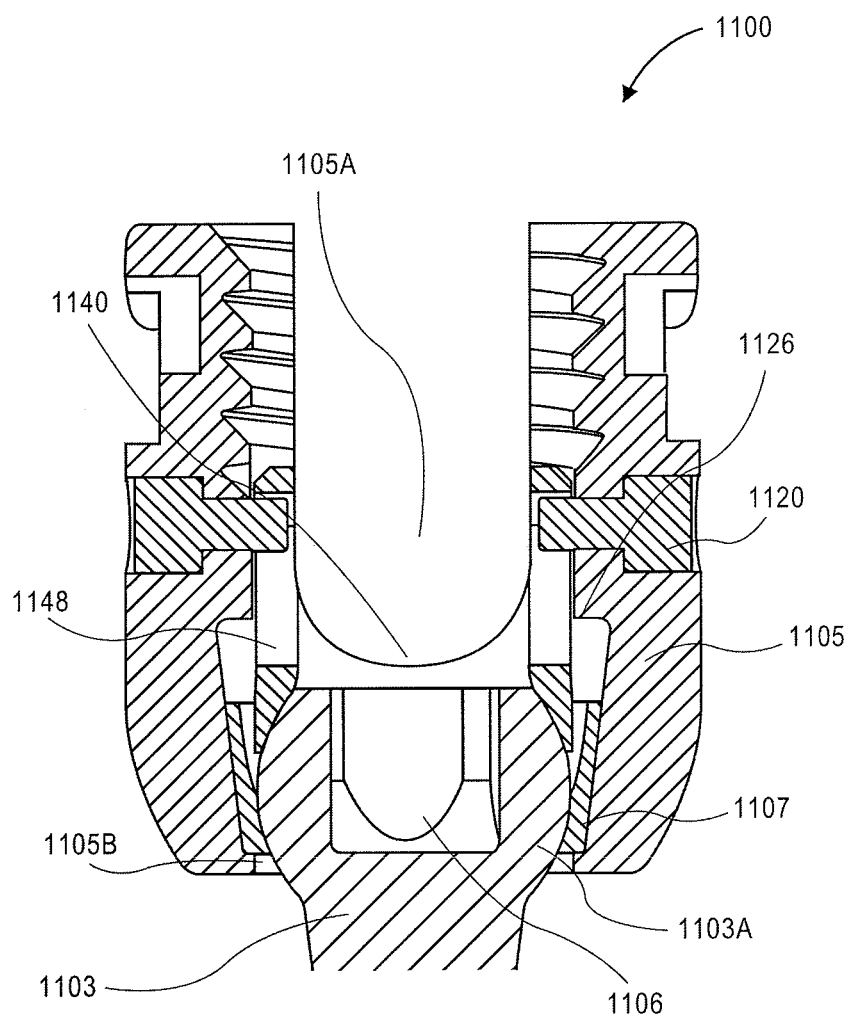
FIG. 11 shows a cross-sectional view of a fastener assembly according to an embodiment of the invention.
Figure 12:
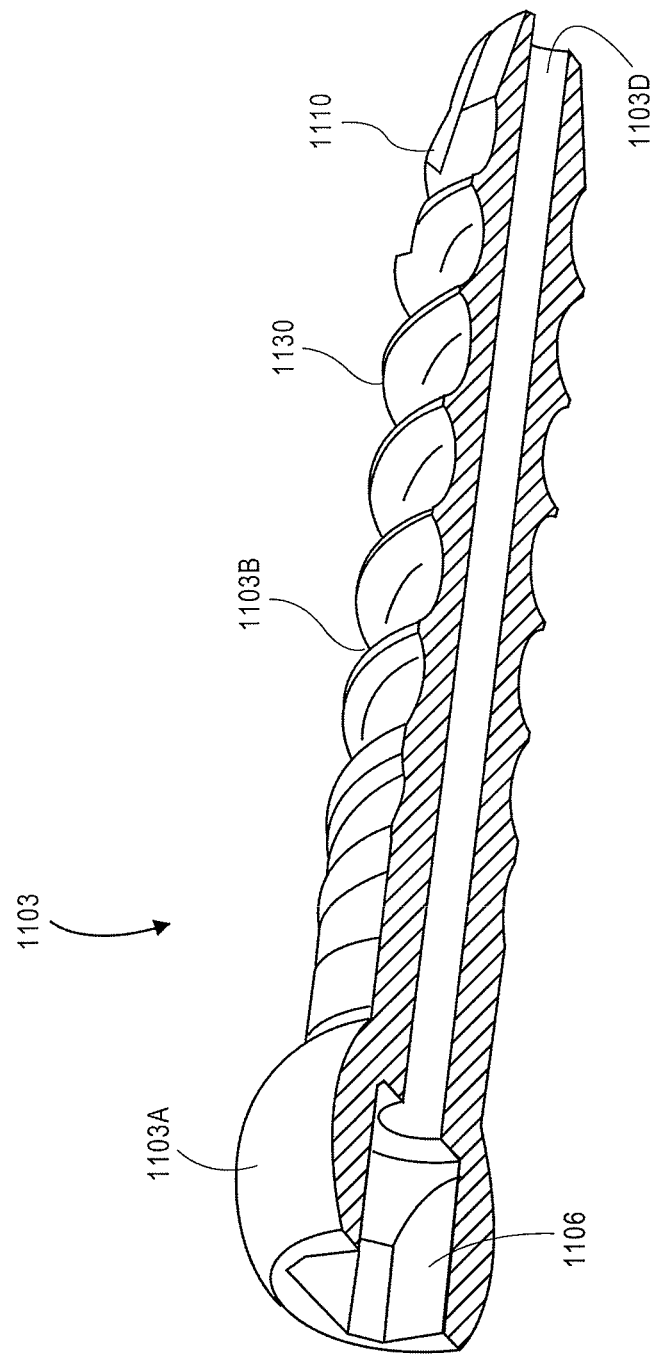
FIG. 12 shows a perspective, cross-sectional view of a fastener according to an embodiment of the invention.

FIG. 11 shows a cross-sectional view of a Fastener Assembly 1100 according to another embodiment of the invention. The Fastener Assembly 1100 may be used in connection with a mounting rod relative to a spine of a patient (of course, one or more such Fastener Assemblies 1100 may be used with one or more rods). More particularly, the Fastener Assembly 1100 may include a Fastener 1103 having a Head 1103A at a first end and a Bone Connection Element 1103B at a second end (FIG. 12). The Head 1103A also includes a Drive Element 1106 (discussed below). The Fastener Assembly 1100 also includes a Body 1105, one or more Pins 1120, a Pressure Cap 1140, a Retention Ring 1107, a Back Wall 1126 of the Fastener Head Receiving Chamber 1105B, a Rod Receiving Channel 1105A, a Line 1148 (illustrates an example length of Pin Receiving Slots 1146 (FIG. 16)) and a Compression Element 109 (not shown). The Compression Element 109 engages the Body 1105, as previously described.

Referring now to FIG. 12, in one embodiment of the present invention, the Fastener 1103 comprises the Head 1103A at a first end and the Bone Connection Element 1103B at a second end (the Bone Connection Element 1103B may be adapted for attachment on, in and/or to the spine). At least a portion of the Head 1103A may be spherical. In other embodiments, the Head 1103A may include a flat surface on a top portion. The Head 1103A further comprises the Drive Element 1106 for engaging a drive tool to attach the Fastener 1103 to the spine. Such a Drive Element 1106 may be an indentation in the Head 1103A shaped to engage a square drive tool, or alternatively any other drive tool having various engaging shapes. The Fastener 1103 may be a bone screw and the Bone Connection Element 1103B may comprise Threads 1130 and a Cannulation 1103D. The Threads 1130 may be of one or more lead designs. The Cannulation 1103D may be used as previously described herein. The tip of the Bone Connection Element 1103B may have Self-Tapping Flutes 1110 that assist the Bone Connection Element to attach to the spine. In one embodiment, there are three Self-Taping Flutes spaced about 120 degrees apart. In other embodiments, there may be two Self-Taping Flutes spaced about 180 degrees apart. Other embodiments can include one or more than three Self-Taping Flutes spaced at appropriate angles.

In other embodiments, the Fastener 1103 may be a bone screw having a standard tip. The Fastener 1103 may further be a non-cannulated bone screw with a tip having a self-tapping feature or a standard tip.

Figure 13:
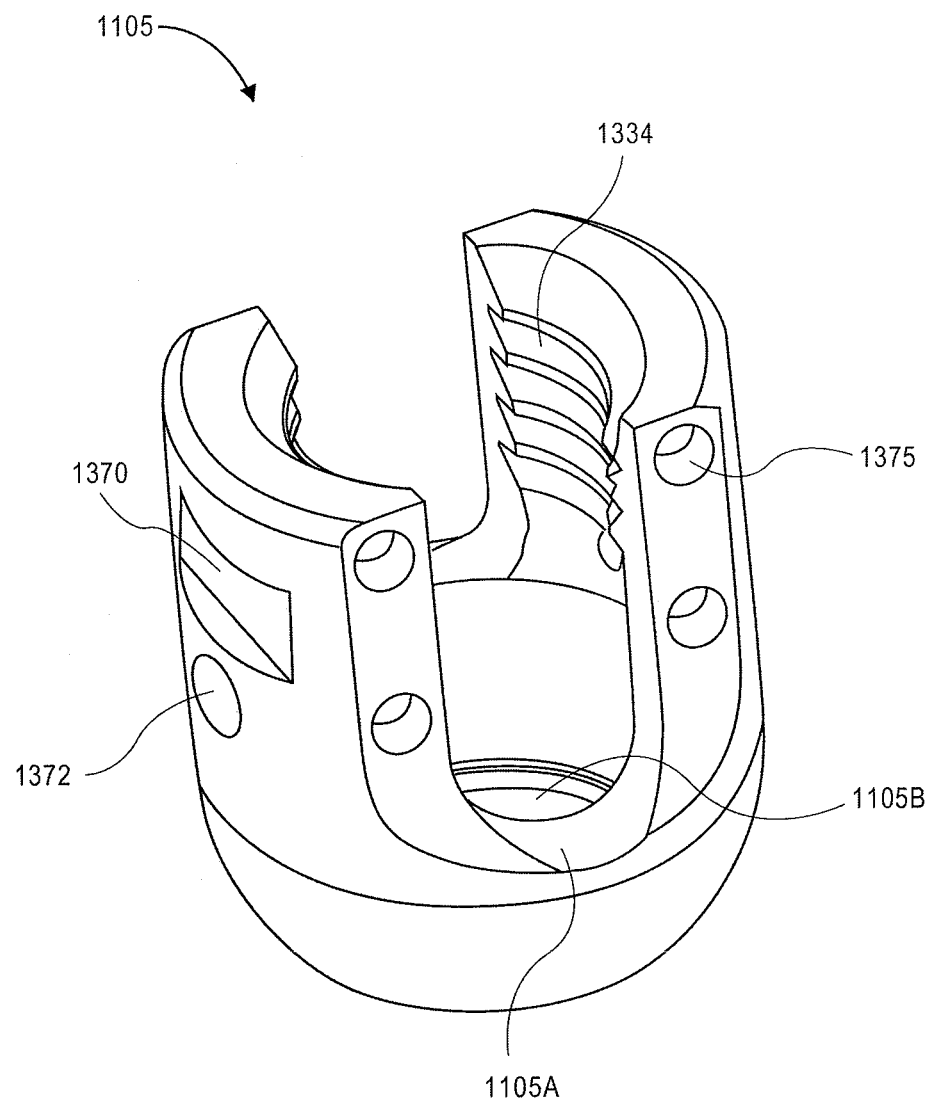
FIG. 13 shows a perspective view of a multi-axial body according to an embodiment of the invention.

Referring now to FIG. 13, the Body 1105 may have a first end and a second end, wherein the Rod Receiving Channel 1105A for receiving the Rod is disposed adjacent the first end of the Body 1105 and the Fastener Head Receiving Chamber 1105B is disposed adjacent the second end of the Body 1105. The Rod Receiving Channel 1105A further includes Threads 1334 for engaging with the Compression Element 109. Other embodiments may forego the Threads 1334 in favor of other lockable means. In this embodiment, the Rod can be inserted at the first end or simply through the Rod Receiving Channel 1105A.

As seen in FIGS. 11 and 13, the Fastener Head Receiving Chamber 1105B may be tapered towards the second end of the Body 1105, and the Rod Receiving Channel 1105A and the Fastener Head Receiving Chamber 1105B may be operatively connected. In one embodiment, the operative connection may be a hole in the Body 1105 of sufficient diameter to allow passage of a drive tool through the hole as described in more detail below. In another embodiment, the Body 1105 maybe a multi-axial body as depicted in FIG. 13 comprising a u-shaped Rod Receiving Channel 1105A. Alternatively, the Body 1105 may comprise other configurations, including but not limited to, a closed body having a Rib 1450 which bridges the two sides of the Rod Receiving Channel 1105A at the first end of the body (see FIG. 14), or a reduction body having Removable Extensions 1560 connected at the first end the body (see FIG. 15).

As further shown in FIG. 13, the Body 1105 may further comprise one or more Pin Mounting Cradles 1332. The Pin Mounting Cradles 1332 may be disposed on either side of the Body 1105 in the walls of the Rod Receiving Channel 1105A. In one embodiment, the Pin Mounting Cradles 1332 are apertures that extend through the entire width of the walls of the Rod Receiving Channel 1105A. The Pin Mounting Cradles can have an outer diameter and an inner diameter, wherein the outer diameter is larger than the inner diameter (FIG. 11). The outer diameter allows the entire Pin 1120 to pass through while the inner diameter allows only a portion of the Pin 1120 to pass through, such as a shaft of the Pin 1120, and not the Pin's head. Additionally, the outer diameter allows the Pins 1120 to be placed flushed against the Body 1105.

Within the Pin Mounting Cradles 1332, Pins 1120 are fixably mounted, such that the Pins 1120 protrude from the Pin Mounting Cradles 1332 into the Rod Receiving Channel 1105A (see FIG. 11). One example method of fixably mounting the Pins 1120 is by welding, however, other means of fixably mounting the Pins 1332 can also be used.

It should be understood by one skilled in the art that the Pin Mounting Cradles 1332 could also be depressions in the inner portions of the walls of the Rod Receiving Channel 1105A, or any other feature that could fixably retain the position of the Pins 1120. Alternatively, the Pins 1120 may just be protrusions from the wall of the Rod Receiving Channel 1105A which are part of the Body 1105 as constructed. The Body 1105 can also include Cut Out 1370 and Holes 1375 located on various surfaces for mating with the Rod reduction and body insertion instrumentation (not shown).

Figure 14:
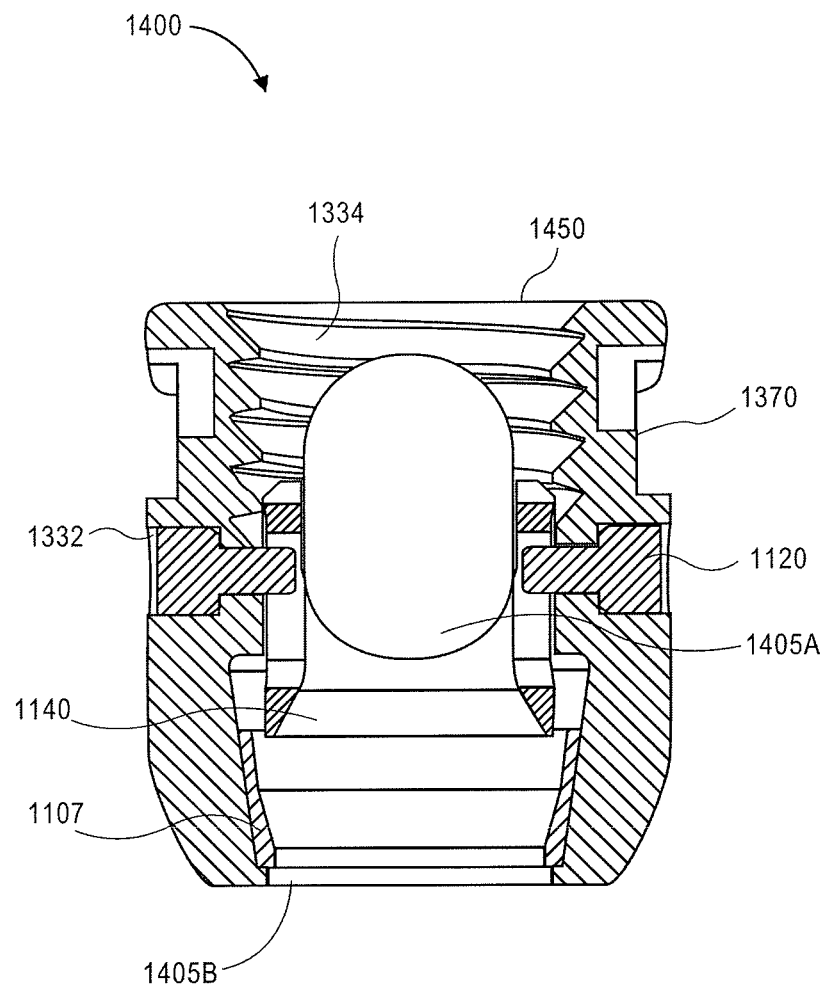
FIG. 14 shows a cross-sectional view of a closed body according to an embodiment of the invention.

FIG. 14 shows a cross-section view of a Closed Body 1400 according to an embodiment of the present invention. The Closed Body 1400 can be essentially the same as the multi-axial body shown in FIG. 13, including the Threads 1334, the Cut Out 1370, Pins 1120, Pin Mounting Cradle 1332, Fastener Head Receiving Chamber 1405B, Pressure Cap 1140, and Retention Ring 1107, but includes Ribs 1450. The Ribs 1450 can be located in the first end of the Closed Body 1400. In this embodiment, the Rod can be inserted through the Rod Receiving Channel 1405A.

Figure 15:
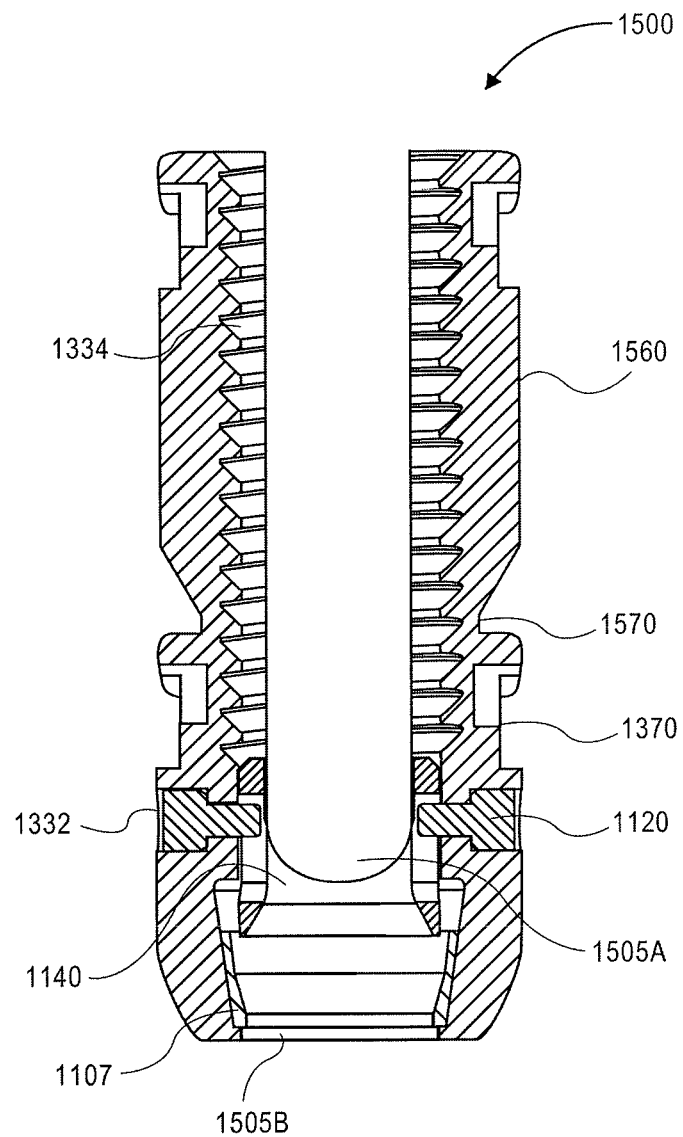
FIG. 15 shows a cross-sectional view of a reduction body according to an embodiment of the invention.

FIG. 15 shows a perspective view of a Reduction Body 1500 according to an embodiment of the present invention. The Reduction Body 1500, like the multi-axial body, includes the Threads 1334, the Cut Out 1370, Pins 1120, Pin Mounting Cradle 1332, Fastener Head Receiving Chamber 1505B, Pressure Cap 1140, and Retention Ring 1107, but further includes a Removable Extensions 1560 and Break Regions 1570. The Removable Extensions 1560 are configured to break off at the Break Regions 1570 after a set screw reduces the Rod into the Body below the Break Region 1570. The Rod Receiving Channel 1505A is elongated so that a set screw engages the Threads 1334 and is threaded down the Removable Extensions 1560 and into the Body 1500 to reduce the Rod for the purposes of aiding deformity correction. Once the Removable Extensions 1560 are broken off then the Reduction Body resembles the multi-axial body 1105.

Figure 16:
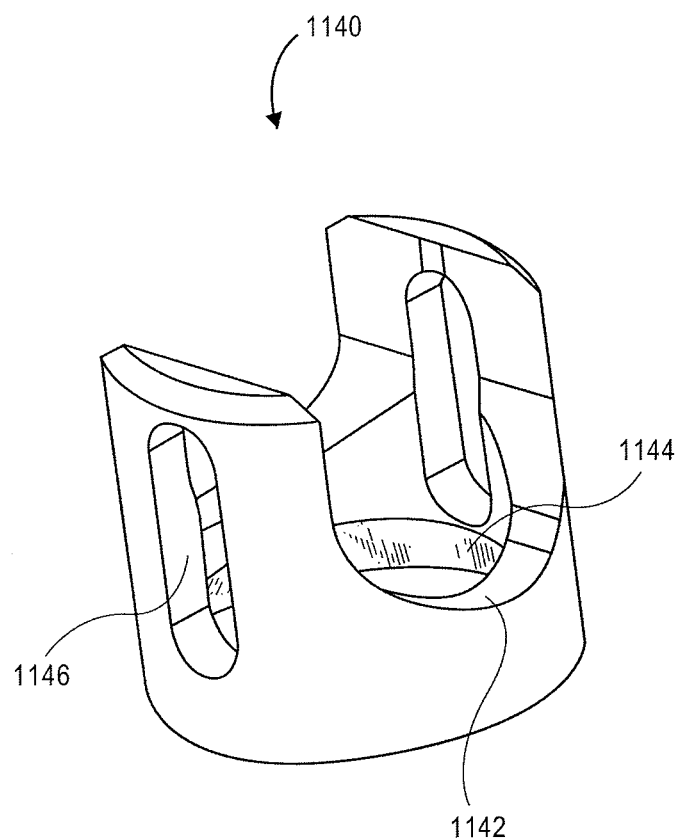
FIG. 16 shows a perspective view of a pressure cap according to an embodiment of the invention.

Now referring to FIG. 16, the Pressure Cap 1140 may have a first end and a second end, wherein a Pressure Cap Rod Receiving Channel 1142 for receiving the Rod is disposed adjacent the first end of the Pressure Cap 1140 and a Head Receiving Face 1144 is disposed adjacent the second end of the Pressure Cap 1140. The Pressure Cap Rod Receiving Channel 1142 may have a "V" shape so as to increase the Rod contact area. As seen in FIG. 16, the Head Receiving Face 1144 may be tapered towards the first end of the Pressure Cap 1140 and form a conical shape. The top end of the conical shape (near the first end of the Pressure Cap) has a smaller diameter than the bottom end (near the second end of the Pressure Cap). Alternatively, the Head Receiving Face 1144 may consist of a partially spherical diameter whose diameter is smaller than that of the Head 1103A of the Fastener 1103. The Pressure Cap Rod Receiving Channel 1142 and the Head Receiving Face 1144 may be operatively connected. In one embodiment, the operative connection may be a hole in the Pressure Cap 1140 of sufficient diameter to allow passage of a drive tool through the hole as described in more detail below.

The Pressure Cap 1140 may comprise one or more Pin Receiving Slots 1146. The Pin Receiving Slots 1146 are disposed on either side of the Pressure Cap 1140 in the walls of the Pressure Cap Rod Receiving Channel 1142. In one embodiment, the Pin Receiving Slots 1146 are apertures that can extend through the entire width of the walls of the Rod Receiving Channel 1142. The Pin Receiving Slots 1146 can run the length of Line 1148 (shown in FIG. 11) of an axis of the Pressure Cap 1140.

As seen in FIG. 11, the Pressure Cap 1140 can be inserted into the Body 1105 such that the first end and the second end of the Body 1105 are adjacent to the first end and second end of the Pressure Cap 1140, respectively. When the Pressure Cap 1140 is inserted into the Body 1105, the Pin Receiving Slots 1146 engage the Pins 1120. The Pin Receiving Slots 1146 are elongated so as to allow the Pressure Cap to slideably move within the Body 1105 between the first end and second end of the Body 1105. Such movement is restricted by contact between the walls of the Pin Receiving Slot 1146 and the Pins 1120. The length of Line 1148 of the Pin Receiving Slots 1146 is such that when the Head 1103A is disposed within the Fastener Head Receiving Chamber 1105B and the Compression Element 109 is tightened, there is clearance between the Pins 1120 and the ends of the Pin Receiving Slots 1146 adjacent to the first end of the Pressure Cap 1140.

It should be understood by one skilled in the art that the Pin Receiving Slot 1146 could also be depressions in the outer portions of the walls of the Pressure Cap Rod Receiving Channel 1142, or any other feature that could slideably engage the Pins 1120.

It should be further noted that is possible for the Pin Mounting Cradles 1332 and the Pins 1120 to reside on the Pressure Cap 1140, with the Pins 1120 protruding from the exterior of the Pressure Cap 1140, and the Pin Receiving Slots 1146 residing on the Body 1105.

Also, other embodiments of each of the Bodies 1105, 1400, 1500 may be sized differently, such that the distance between the Rod Receiving Channel 1105A, 1405A, 1505A, respectively, and the Fastener Head Receiving Chamber 1105B, 1405B, 1505B, respectively, varies between the embodiments. In such embodiments, the Pressure Cap 1140 may be appropriately size by varying the distance between the Pressure Cap Rod Receiving Channel 1142 and the Head Receiving Face 1144 so that the Pressure Cap 1140 may function as described in connection with previous embodiments.

Figure 17:
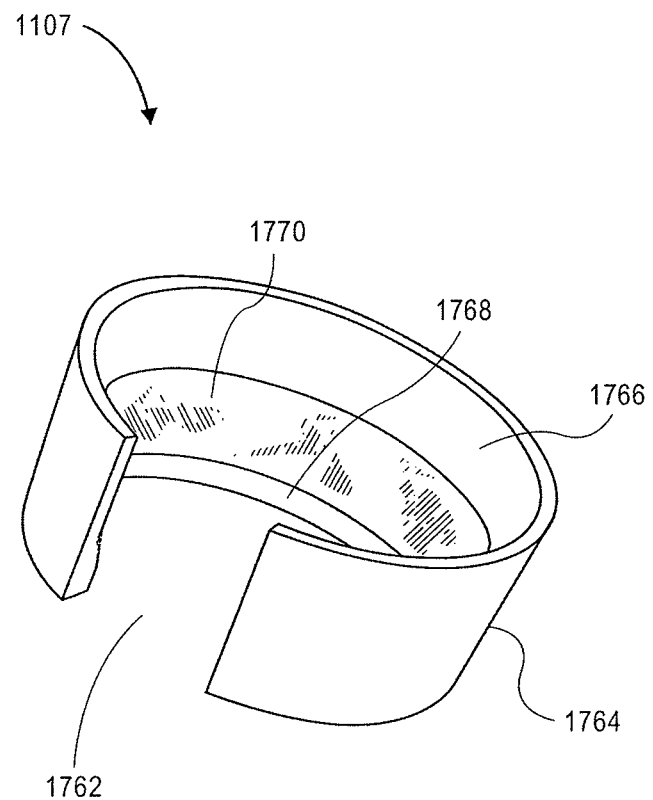
FIG. 17 shows a perspective view of a retention ring according to an embodiment of the invention.

Further, Fastener Assembly 1100 of FIG. 11 may include the Retention Ring 1107. This Retention Ring 1107 may be constructed to fit at least partially around the Head 1103A when the Head 1103A is disposed within the Fastener Head Receiving Chamber 1105B. When the Retention Ring 1107 is fitted around the Head 1103A, the Retention Ring 1107 expands and contracts such that the Head 1103A cannot be extracted from the Fastener Head Receiving Chamber 1105B through the second end of the Body 1105. In one embodiment, the Retention Ring 1107 may be, as shown in the FIG. 17, of a "split-ring" design. The Retention Ring 1107 may comprise a first end and a second end where a Slit 1762 extends fully between both ends. Further the Exterior Wall 1764 of the Retention Ring 1107 may taper from the first end to the second end having a substantially similar taper to that of the Fastener Head Receiving Chamber 1105B. The Retention Ring 1107 may further comprise an Upper Inner Taper 1766 adjacent to the first end, which has a taper substantially similar to the taper of the Exterior Wall 1764, a Cylinder 1768 adjacent to the second end, and a Lower Inner Taper 1770 disposed between the Upper Inner Taper 1766 and the Cylinder 1768, having a taper greater than that of the Upper Inner Taper 1766.

In operation, the Compression Element 109 may cooperate with the Body 1105 to push a Rod, when the Rod is disposed within the Rod Receiving Channel 1105A, into contact with at least part of the Pressure Cap Rod Receiving Channel 1142. Such contact between the rod and the Pressure Cap Rod Receiving Channel 1142 will slideably move the Pressure Cap 1140 causing the Head Receiving Face 1144 to press the Head 1103A towards the tapered end (i.e., narrower end) of the Fastener Head Receiving Chamber 1105B. This action will serve to fix the angular relationship of Fastener 1103 relative to the rod.

More particularly, the angular relationship of Fastener 1103 relative to the Rod may be fixed at least in part due to: (a) an interference fit (caused by radial compression) between at least a portion of an outside surface of Head 1103A and at least a portion of an inside surface of Retention Ring 1107; (b) an interference fit (caused by radial compression) between at least a portion of an outside surface of Retention Ring 1107 and at least a portion of an inside surface of Fastener Head Receiving Chamber 1105B; and/or (c) an interference fit between at least a portion of the Head Receiving Face 1144 and an outside surface of Head 1103A.

Figure 23:
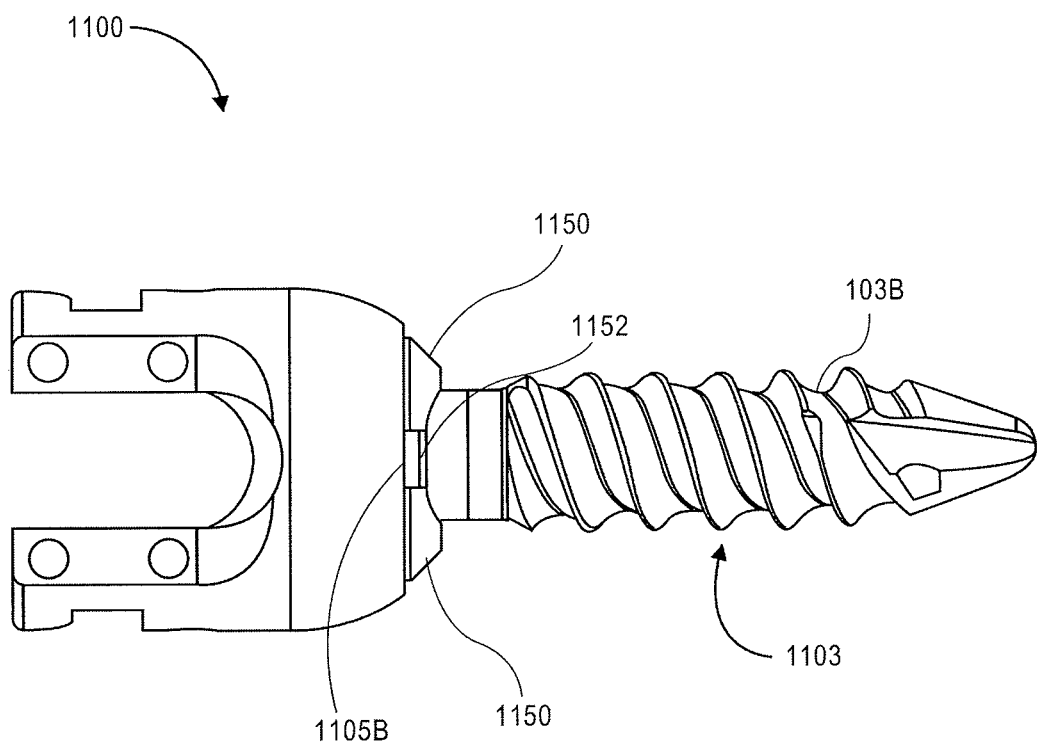
FIG. 23 shows an elevation view of a flange according to an embodiment of the invention.

Another embodiment of the Fastener Assembly 1100, as seen in FIG. 23, may include the attachment of a Flange 1150 at the opening of the Fastener Head Receiving Chamber 1105B. The Flange 1150 may be a single piece including a Flange Slot 1152. The single piece may be of any shape, for example, circular or U-shaped, or it may comprise multiple pieces, any of which, when attached to the Fastener Assembly 1100 create a Flange Slot 1152. The Flange Slot 1152, may be a hole in the Flange 1150 or a space between pieces of the Flange 1150. The Bone Connection Element 103B of the Fastener 1103 may extend through the Flange Slot 1152. The Flange 1150 may be attached in a variety of ways, including, for example, welding, gluing, or attaching via a connection element, before or after inserting the Fastener 1103 into the Fastener Head Receiving Chamber 1105B. The Flange 1150 may restrict the angular relationship of Fastener 1103 relative to the Rod by limiting the movement of the Fastener 1103 to one plane coinciding with the Flange Slot 1152.

Figure 24:
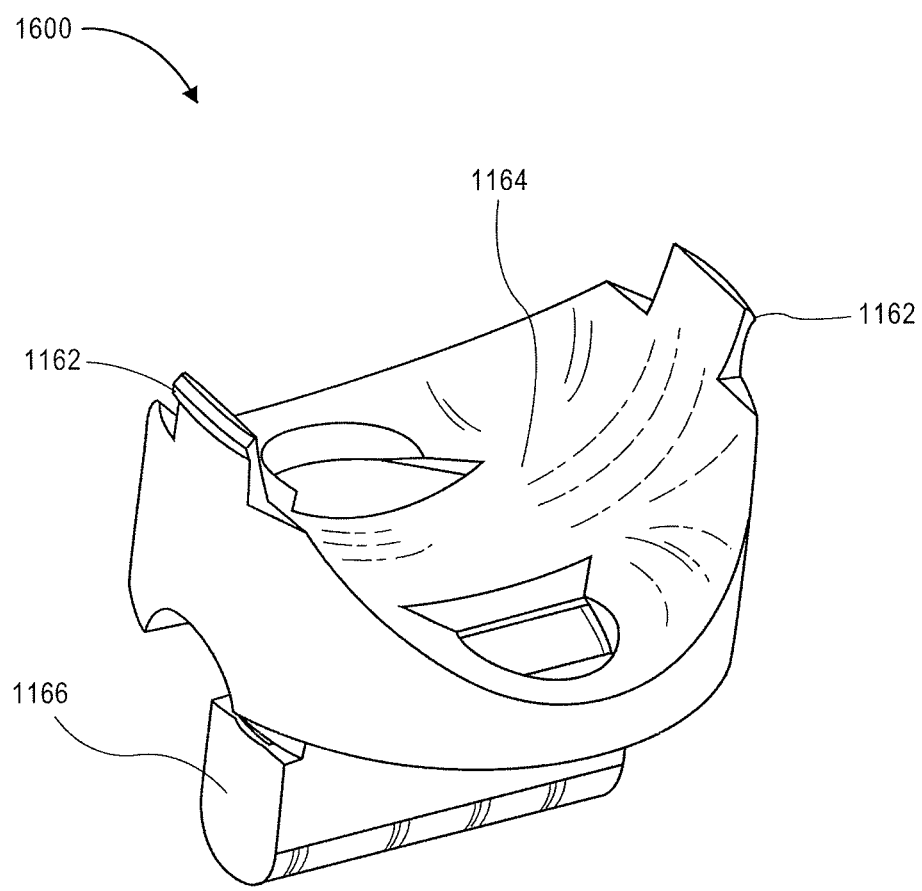
FIG. 24 shows a perspective view of an orientation plug according to an embodiment of the invention.

Still another embodiment, as seen in FIG. 24, may include an Orientation Plug 1160 to restrict the angular relationship of Fastener 1103 relative to the Rod. The Orientation Plug 1160 may have an Engagement Feature 1162, a Rod Receiving Face 1164, and a Projection 1166. The Engagement Feature 1162 may be shaped to engage with the Pin Receiving Slots 1146 (shown in FIG. 16) of the Pressure Cap 1140. The Rod Receiving Face 1164 may be shaped similarly to the Pressure Cap Rod Receiving Channel 1142 (shown in FIG. 16) so that it may contact the Rod but not interfere with the contact between the Rod and the Pressure Cap Rod Receiving Channel 1142. The Projection 1166 may be shaped such that it contacts the Drive Element 1106 (shown in FIG. 12) of the Fastener 1103, limiting the movement of the Fastener in at least one direction.

Reference will now be made to the elements shown in FIG. 11 in connection with the description of an example installation procedure. Such an example installation procedure is applicable to this embodiment of the fastener assembly of the present invention and, of course, is intended to be illustrative and not restrictive.

More particularly, a guide wire may first be attached to a pedicle of the spine. The free end of the guide wire may then be passed through the Fastener 1103 (via the Cannulation 1103D (FIG. 12)). The Fastener 1103 (e.g., a pedicle screw) may then be inserted (e.g., screwed into) into the pedicle of the spine. Of note, such a pedicle screw may be self-tapping into a hole bored into the pedicle or the hole bored into the pedicle may be pre-tapped. Of further note, such a pedicle screw may be driven into bone with any desired tool (e.g., a hand or power driver applying torque through the hole provided in the Body 1105 between the Rod Receiving Channel 1105A and the Fastener Head Receiving Chamber 1105B, and the hole provided in the Pressure Cap 1140 between the Pressure Cap Rod Receiving Channel 1142 and the Head Receiving Face 1144).

In one embodiment, such a pedicle screw may be driven into bone with a torque applying drive tool that engages one or more indentations, protrusions and/or drive faces on the Head 1103A (see, e.g., Drive Element 1106 of Head 1103A in FIG. 12).

In one embodiment, the Fastener 1103 may be driven into bone by itself. Next, a body/retention device/pressure cap assembly (e.g., including the Body 1105 having the Retention Ring 1107 already disposed within the Fastener Head Receiving Chamber 1105B, the Pins 1120 already fixably disposed within the Pin Mounting Cradles 1332, and the Pressure Cap 1140 already slideably engaged on the Pins 1332) may be placed (or "snapped") onto Fastener 1103.

In this regard, as the Body 1105 is subsequently pushed onto the Head 1103A (or vice-versa), the Retention Ring 1107 is pushed against the Back Wall 1126 (see FIG. 11) of the Fastener Head Receiving Chamber 1105B and the Retention Ring 1107 is free to expand outward enabling the Head 1103A to pass through. Once the Head 1103A pushes through the bottom of the Retention Ring 1107, the Head 1103A remains captured (since the Retention Ring 1107 would have no room to expand as it was pulled forward by the Head 1103A towards the tapered (i.e., narrowed) end of the Fastener Head Receiving Chamber 1105B.

Simultaneously, as the Head 1103A passes through the Retention Ring 1107, the Head 1103A contacts the Head Receiving Face 1144 (shown in FIG. 16) and slideably pushes the Pressure Cap 1140 toward the first end of the Body 1105. The length of the Pin Receiving Slots 1146 (shown in FIG. 16) is such that when the Head 1103A is inserted into the Fastener Receiving Chamber 1105B, there is enough clearance between the ends of the Pin Receiving Slots 1146 and Pins 1120 to allow for assembly.

Next, the rod may be placed in the Rod Receiving Channel 1105A and the Pressure Cap Rod Receiving Channel 1142 (shown in FIG. 16).

Finally, as the Compression Element 109 (e.g., a set screw) is threaded into the Body 1105, the Compression Element 109 clamps the components in a set position. That is, the Compression Element 109 pushes the rod against the Pressure Cap Rod Receiving Channel 1142 (shown in FIG. 16), which pressure slideably pushes the Pressure Cap 1140 toward the second end of the Body 1105. Then the Head Receiving Face 1144 pushes the Head 1103A against the Retention Ring 1107, which in turn pushes against the tapered inner walls of the body. Of note, during this clamping process the movable nature of the Pressure Cap 1140 allows for some clearance between the Pins 1120 and Pin Receiving Slots 1146 (shown in FIG. 16) enabling clamping of the Head 1103A to take place.

If using the Flange 1150, it may be attached to the Fastener Assembly 1100 at any point after the Body 1105 is pushed onto the Head 102 (or vice-versa). Further, if using the Orientation Plug 1160, it may be inserted into the Fastener Assembly 1100 at any point before inserting the Rod.

In another embodiment, it is possible, rather than driving Fastener 1103 into bone by itself and then placing a body/retention ring/pressure cap assembly thereon, the Fastener 1103 may be captured within body/retention ring/pressure cap assembly as discussed above and then the entire body/retention ring/pressure cap/fastener assembly may be attached to the bone (e.g., by using a driving tool such as a hand or power driver to drive the pedicle screw through the hole provided in the Body 1105 between the Rod Receiving Channel 1105A and the Fastener Head Receiving Chamber 1105B, and the hole provided in the Pressure Cap 1140 between the Pressure Cap Rod Receiving Channel 1142 and the Head Receiving Face 1144).

In this embodiment, if using the Flange 1150, it may be attached to the Fastener Assembly 1100 at any point, for example, the manufacturer may connect the Flange 1150 to the Fastener Assembly 1100. If the Orientation Plug 1160 is used, then its insertion into the Fastener Assembly 1100 must wait until after the Fastener is driven into the bone.

Another embodiment (not shown) of the present invention is similar to the embodiment shown in FIG. 11 and, in this regard, the same elements will be identified by the same reference numerals (such similar elements will not be described again in detail). The difference between the embodiments is that in this embodiment the Fastener Assembly 1100 does not utilize Retention Ring 1107, and that the tapered (i.e., narrow) end of the Fastener Head Receiving Chamber 1105B may be made sufficiently small so as to prohibit the Head 1103A from passing therethrough (while the Rod Receiving Channel 1105A, the hole in the Body 1105 connecting the Rod Receiving Channel 1105A to the Fastener Head Receiving Chamber 1105B, may be made sufficiently large so as to allow Head 1103A to pass therethrough).

It is further envisioned that the angular relationship of Fastener 1103 relative to the Rod may be restricted by the shape of the opening of the tapered end of the Fastener Head Receiving Chamber 1105B through which extends the Fastener 1103. An example (not shown) of such an opening may be shaped like a slot, and the movement of the Fastener 1103 may be restricted to a single plane coinciding with the slot. The Fastener Head Receiving Chamber 1105B may also be extend to encompass more of the Bone Connection Element 103B to greater restrict the movement of the Fastener 1103.

In this regard, the Fastener Assembly 1100 may be installed by inserting the Fastener 1103 through the Body 1105, such that the Head 1103A comes to rest in the Fastener Head Receiving Chamber 1105B. The Pressure Cap 1140 is the inserted into the Body 1105, and the Fastener 1103 may then be inserted (e.g., into the pedicle of the spine) as discussed above (e.g., a guide wire may be used to guide the Fastener 1103 and either a self-tapping bone screw may be driven into a hole in the bone or a pre-tapped hole in the bone may be provided).

Finally, the Compression Element 109 may cooperate with the Body 1105 to push the rod, when the rod is disposed within the Rod Receiving Channel 1105A, into contact with at least part of the Pressure Cap Rod Receiving Channel 1142 to slideably move the Pressure Cap 1140 while pressing the Head 1103A towards the tapered end (i.e., narrower end) of the Fastener Head Receiving Chamber 1105B. This action will fix the angular relationship of Fastener 1103 relative to the rod (the angular relationship of the Fastener 1100 relative to the rod may be fixed at least in part due to: (a) an interference fit (caused by radial compression) between at least a portion of an outside surface of the Head 1103A and at least a portion of an inside surface of the Fastener Head Receiving Chamber 1105B; and/or (b) an interference fit between at least a portion of an outside surface of at least a portion of an outside surface of the Head 1103A and the Head Receiving Face 1144).

Figure 18:
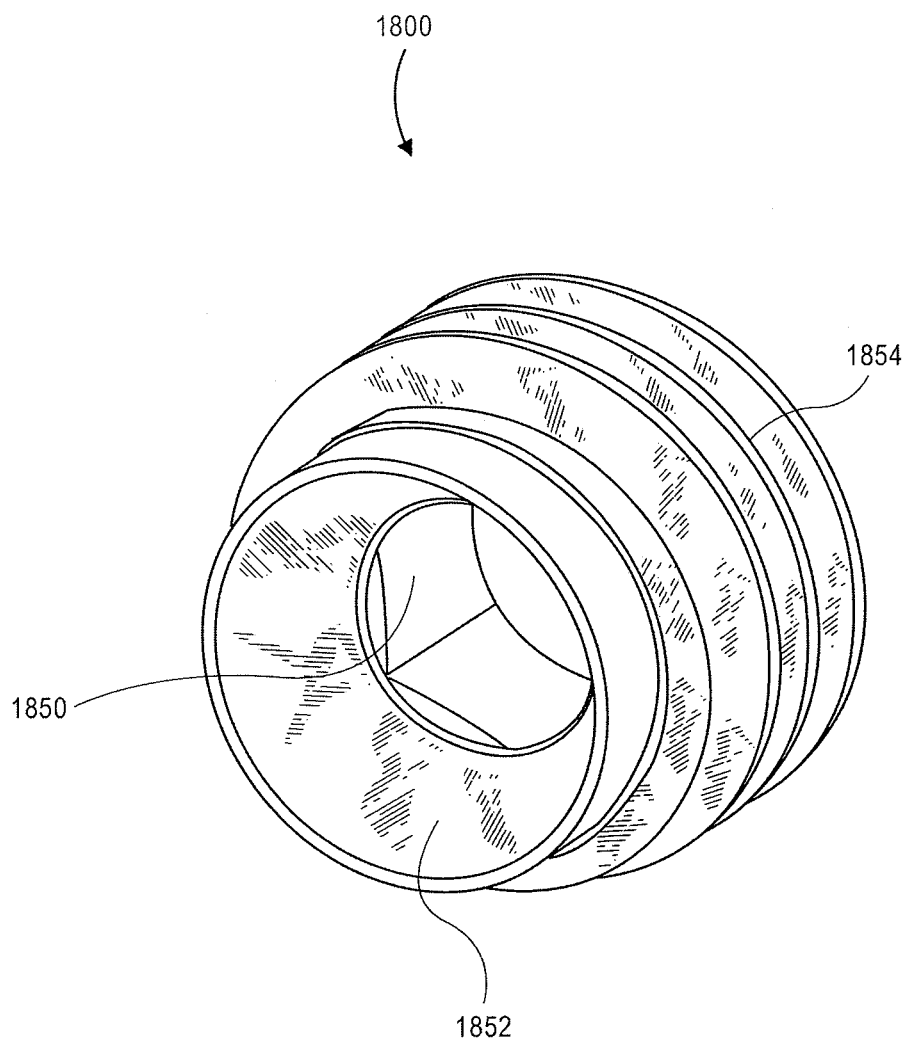
FIG. 18 shows a perspective view of an offset set screw according to an embodiment of the invention.

Referring now to FIG. 18, an Offset Set Screw 1800 has a first end and a second end, wherein an Offset Drive Feature 1850 is disposed adjacent to the first end of the Offset Set Screw 1800 and an Offset Head Receiving Face 1852 is disposed adjacent to the second end of the Offset Set Screw 1800. The Offset Head Receiving Face 1852 may be tapered toward the first end of the Offset Head Receiving Face 1852 along an inner surface and forms a conical shape inner surface. The conical shape inner surface is constructed and designed to receive the Head 1103A of Fastener 1103. Alternatively, the Offset Head Receiving Face 1852 may consist of a partially spherical diameter whose diameter is smaller than that of the Head 1103A of the Fastener 1103.

In one embodiment, the diameter of the Offset Head Receiving Face 1852 at the first end is larger than the diameter at the second end and in another embodiment, the diameter of the Offset Head Receiving Face 1852 at the first end is less than the diameter at the second end. The Offset Drive Feature 1850 and the Offset Head Receiving Face 1852 may be operatively connected through a hole in the Offset Set Screw 1800. Threads 1854 are configured to engage the threads of Offset Fastener Assembly 2000, described below.

In an alternative embodiment, the Offset Set Screw 1800 may be comprised of multiple pieces. One such embodiment may include a first piece, which may embody the Offset Head Receiving Face 1852, to contact the Head 1103A of Fastener 1103, and a second piece, such as the Compression Element 109 (which may embody a set screw), to lockably retain the first piece. The first piece may be placed in or threaded into the Offset Fastener Head Receiving Chamber 2022 of the Offset Fastener Assembly 2000, described below, and the second piece may be fastened into the Offset Fastener Head Receiving Chamber 2022 retaining the first piece in place.

Figure 19:
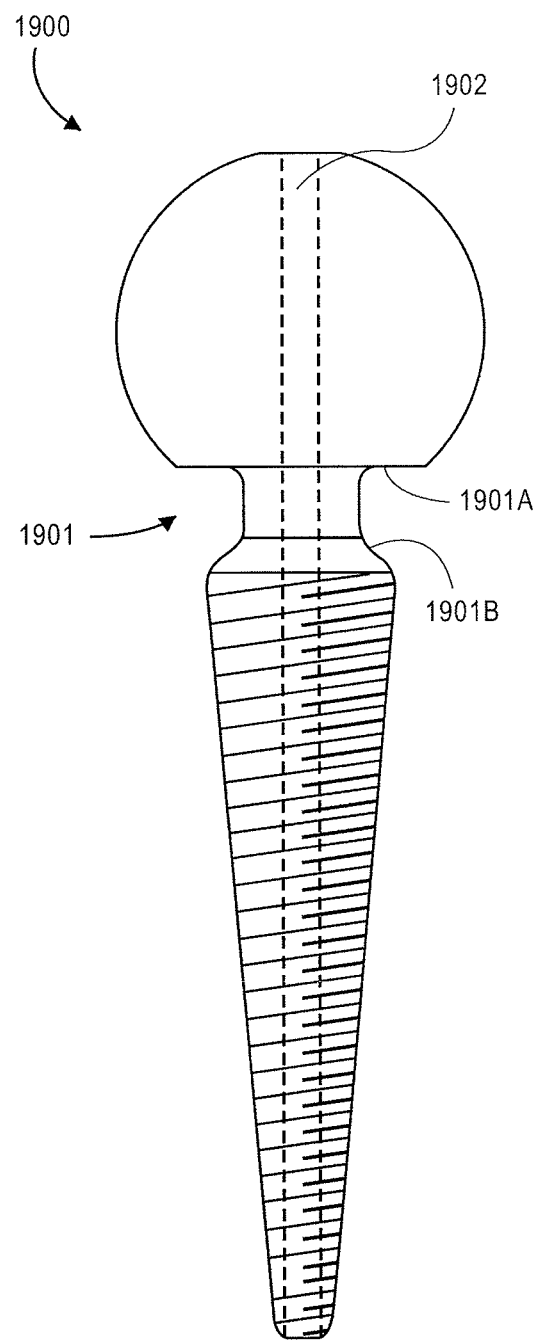
FIG. 19 shows a side view of an alternative fastener according to an embodiment of the invention.

Referring now to FIG. 19, wherein another embodiment of a Fastener 1900 for use with the invention is shown. The Fastener 1900 is depicted here as a bone screw, although other types of bone attaching mechanisms may, of course, be utilized (e.g., a shaft having a hook on the end). In any case, it is seen that in this embodiment an Undercut 1901 is provided and may be formed, for example, by providing a Bottom of the Head 1901A of the head of the bone screw and/or by providing a Shaft 1901B of the bone screw. By using such an Undercut 1901, the Fastener 1900 may provide increased clearance in the area where the Fastener 1900 extends from the body of the Fastener Assembly 1100, wherein such increased clearance may translate into an increase in a maximum angle that the Fastener 1900 may obtain in relation to the fastener body and/or the rod. Cannulation 1902 is also shown in FIG. 19 for the purposes previously described.

Figure 20:
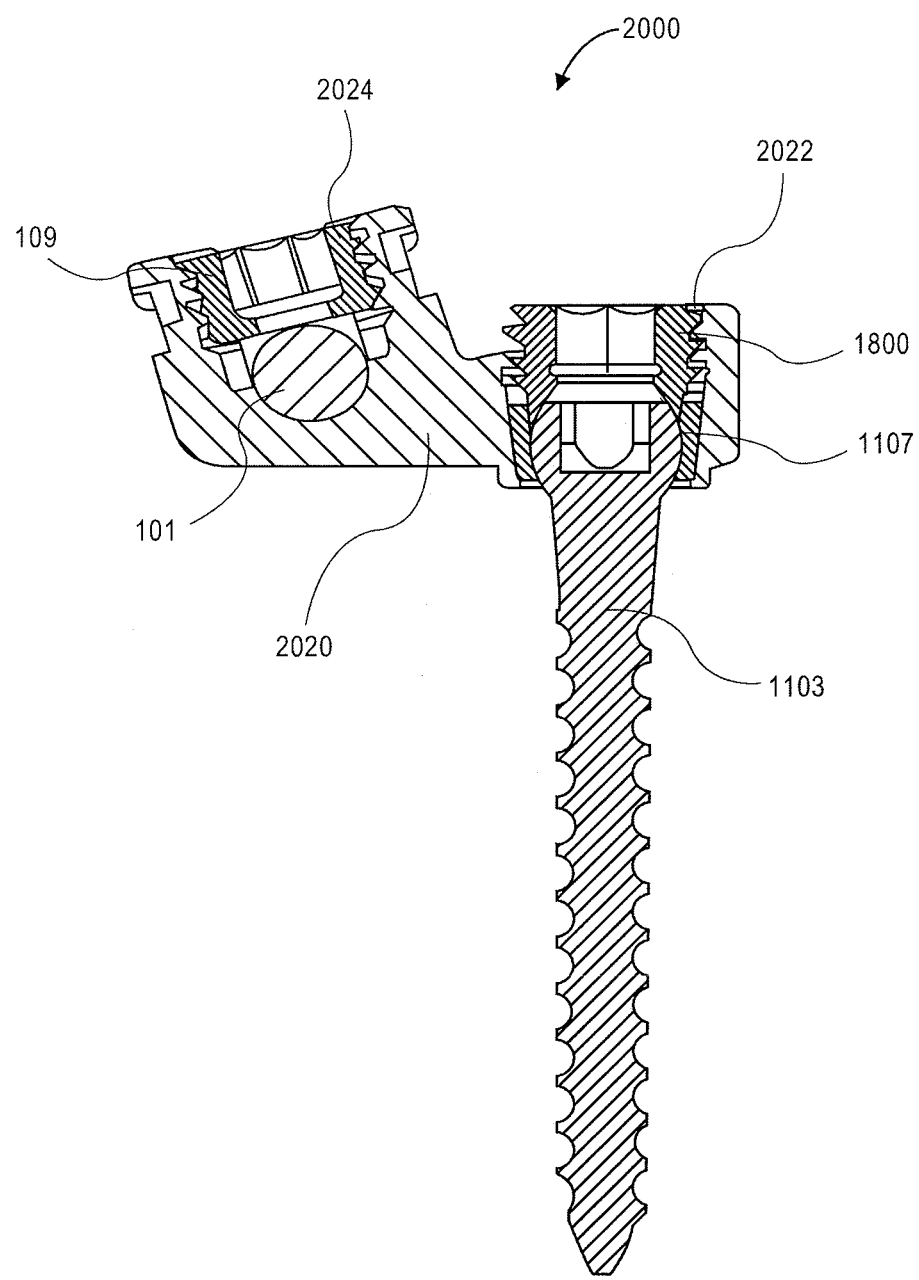
FIG. 20 shows a cross-sectional view of an offset fastener assembly according to an embodiment of the invention.

Referring now to FIG. 20, an alternative embodiment of the invention is shown. The Offset Fastener Assembly 2000 may be used in connection with a Rod 101 relative to a spine of a patient (of course, one or more such Fastener Assemblies may be used with one or more rods). More particularly, the Offset Fastener Assembly 2000 may include the Fastener 1103, an Offset Body 2020, Offset Set Screw 1800, Retention Ring 1107, and the Compression Element 109.

The Offset Body 2020 includes a lateral offset (e.g., an 8 mm, 11 mm, or 14 mm lateral offset) between the Offset Fastener Head Receiving Chamber 2022 and the Offset Rod Receiving Channel 2024. Further, the Offset Rod Receiving Channel 2024 is angled (e.g., 15 degrees, 25 degrees, or 50 degrees) from vertical (and from a vertical axis disposed through the Offset Fastener Head Receiving Chamber 2022). It is envisioned that the lateral offset between the Offset Fastener Head Receiving Chamber 2022 and the Offset Rod Receiving Channel 2024 is not limited to the example distances above, and that the distance of the offset may be of any length. It is further envisioned that the angle of the Offset Rod Receiving Channel 2024 is not limited to the example angles above, and that the angle may be of any degree and in any direction.

Another embodiment (not shown) of the Offset Fastener Assembly 2000 may include the attachment of a Flange at the opening of the Offset Fastener Head Receiving Chamber 2022. The Flange may be a single piece including a Flange Slot. The single piece may be of any shape, for example, circular or U-shaped, or it may comprise multiple pieces that when attached to the Offset Fastener Assembly 2000 to create the Flange Slot. The Bone Connection Element 103B of the Fastener 1103 may extend through the Flange Slot. The Flange may be attached in a variety of ways, including, for example, welding, gluing, or attaching via a connection element, before or after inserting the Fastener 1103 into the Offset Fastener Head Receiving Chamber 2022. The Flange may restrict the angular relationship of Fastener 1103 relative to the Rod by limiting the movement of the Fastener 1103 to one plane coinciding with the Flange Slot.

Such offset design may be used in a manner similar to that described with respect to the non-offset designs (e.g., the Body 1105) disclosed herein. FIG. 20 depicts one such embodiment where the Compression Element 109, such as a set screw, may be used to fix the Rod 101 relative to the Offset Body 2020 and the Offset Set Screw 1800 may be used to fix the Fastener 1103 relative to the Body.

Of further note, the offset designs may ease assembly of the fixation system (e.g., by providing a surgeon laterally offset/angled options when connecting the spinal rod(s)).

Figure 21:
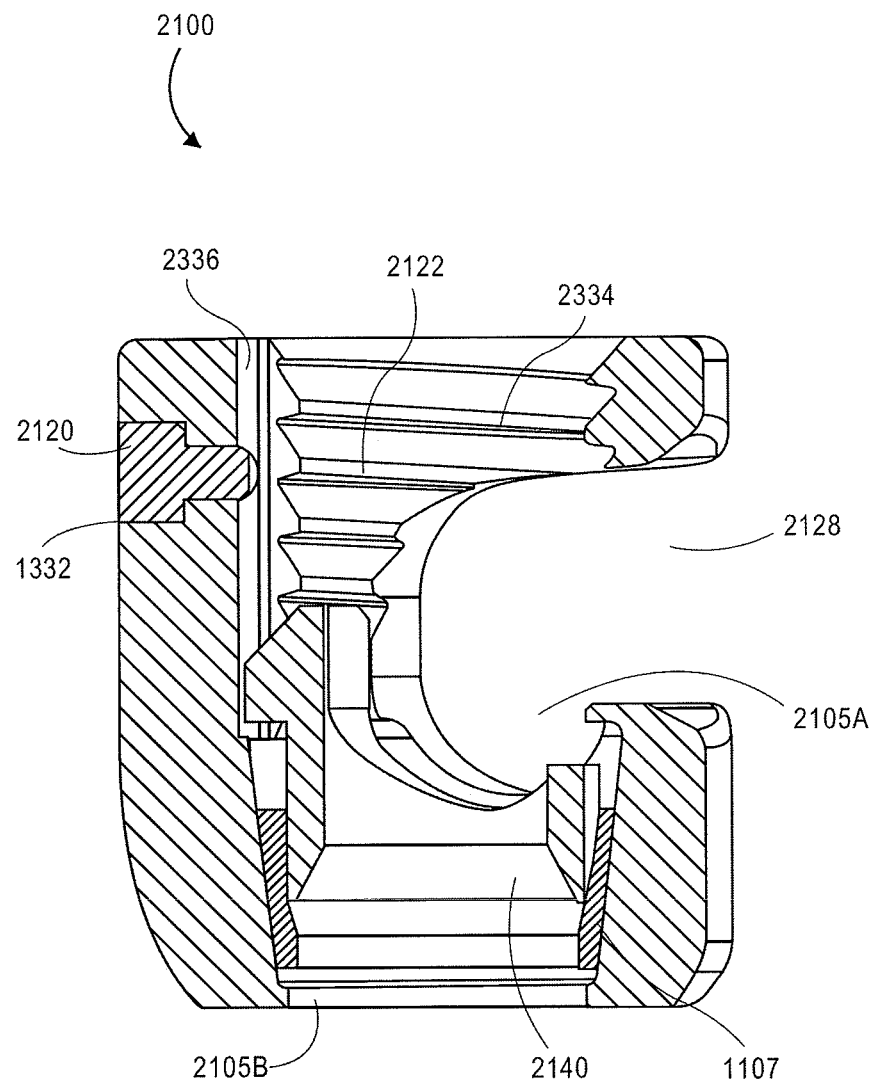
FIG. 21 shows a cross-sectional, perspective view of a body according to an embodiment of the invention.

Referring now to FIG. 21, another embodiment of the Fastener Assembly 1100 may comprise a Body 2100. The Body 2100 may have a first end and a second end, wherein a Compression Element Receiving Chamber 2122 is disposed adjacent the first end of the Body 2100 and a Fastener Head Receiving Chamber 2105B is disposed adjacent the second end of the Body 2100. A Rod Receiving Channel 2105A for receiving the Rod is disposed between the Compression Element Receiving Chamber 2122 and Fastener Head Receiving Camber 2105B. The Compression Element Receiving Chamber 2122 further includes Threads 2334 for engaging with the Compression Element 109. The Threads 2334 incorporate a Tab Channel 2336 to allow a Pressure Cap 2140 to slideably move within Body 2100. In this embodiment, the Rod can be inserted through an Opening 2128 in a wall of the Body 2100 or simply through the Rod Receiving Channel 2105A.

As seen in FIG. 21, the Fastener Head Receiving Chamber 2105B may be tapered towards the second end of the Body 2100, and the Compression Element Receiving Chamber 2122, the Rod Receiving Channel 2105A, and the Fastener Head Receiving Chamber 2105B may be operatively connected. In one embodiment, the operative connection may be a hole in the Body 2100 of sufficient diameter to allow passage of a drive tool through the hole as described herein. Further a Retention Ring 1107 may be disposed within the Fastener Head Receiving Chamber 2105B.

The Body 2100 may further comprise at least one Pin Mounting Cradle 1332 to fixably retain a Pin 2120. The Pin Mounting Cradle 1332 is disposed on a side of the Body 2100 in a wall of the Rod Receiving Channel 2105A or a wall of the Compression Element Receiving Chamber 2122. In one embodiment, the Pin Mounting Cradle 1332 is an aperture that extends through the entire width of the wall of a Tab Channel 2336. The Pin Mounting Cradle 1332 and the Pin 2120 are otherwise substantially similar to the Pin Mounting Cradle 1332 and the Pin 1120 (shown in FIG. 11) as described above, except that Pin 2120 is sized such that it does not extend into the Compression Element Receiving Chamber 2122 so that it does not interfere with the insertion of the Compression Element 109.

Figure 22:
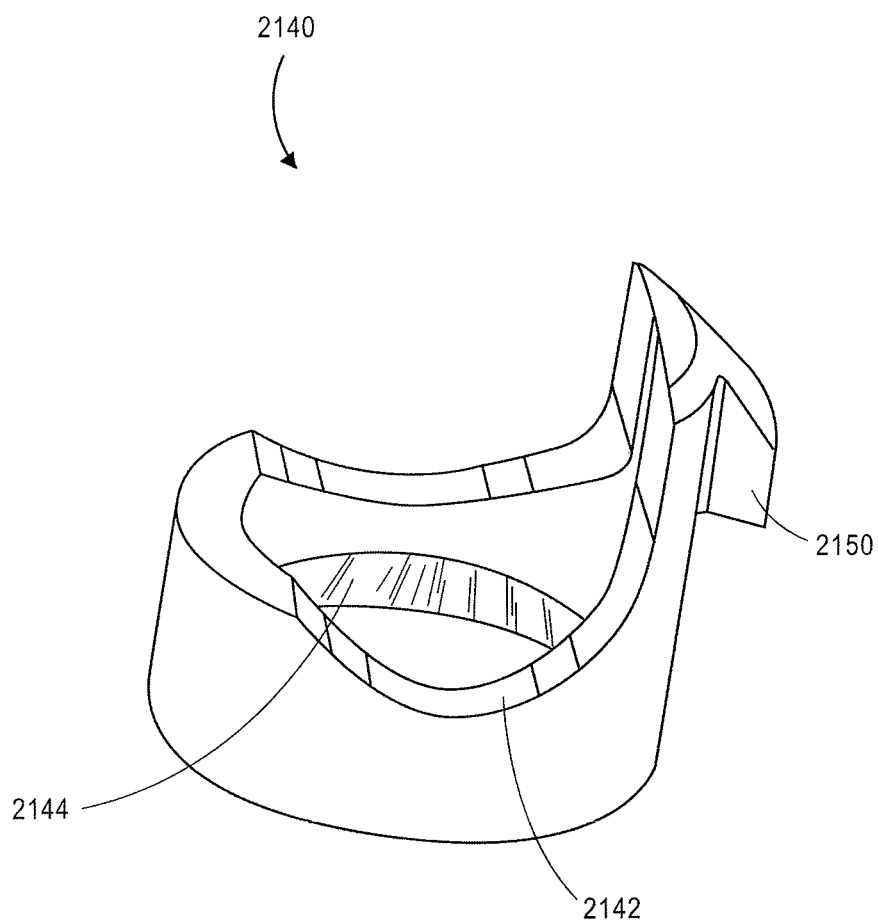
FIG. 22 shows a perspective view of a pressure cap according to an embodiment of the invention.

Now referring to FIG. 22, the Pressure Cap 2140 may have a first end and a second end, wherein a Pressure Cap Rod Receiving Channel 2142 for receiving the rod is disposed adjacent the first end of the Pressure Cap 2140 and a Head Receiving Face 2144 is disposed adjacent the second end of the Pressure Cap 2140. As seen in FIG. 22, the Head Receiving Face 2144 may be tapered towards the first end of the Pressure Cap 2140, and the Pressure Cap Rod Receiving Channel 2142 and the Head Receiving Face 2144 may be operatively connected. In one embodiment, the operative connection may be a hole in the Pressure Cap 2140 of sufficient diameter to allow passage of a drive tool through the hole as described herein.

The Pressure Cap 2140 further comprises a Guide Tab 2150. In one embodiment the Guide Tab 2150 is disposed within the Tab Channel 2336.

As seen in FIG. 21, the Pressure Cap 2140 can be inserted into the Body 2100 such that the first end and the second end of the Body 2100 are adjacent to the first end and second end of the Pressure Cap 2140, respectively. When the Pressure Cap 2140 is inserted into the Body 2100, the Tab Channel 2336 engages the Guide Tab 2150. The Tab Channel 2336 is elongated so as to allow the Pressure Cap 2140 to slideably move within the Body 2100 between the first end and second end of the Body 2100. Such movement is restricted by contact between the walls of the Tab Channel 2336 and a Pin 2120 with the Guide Tab 2150. The length dimension of the Tab Channel 2336 is such that when the Head 1103A is disposed within the Fastener Head Receiving Chamber 2105B, and the Compression Element 109 is tightened, the Guide Tab 2150 does not come in contact with the Pin 2120. Further, the length of the Tab Channel 2336 is such that when the Head 1103A is inserted into the Fastener Receiving Chamber 2105B, there is enough clearance between the Guide Tab 2150 and the Pin 2120 to allow for assembly.

Assembly and use of this embodiment of the Fastener Assembly 1100 is substantially similar as to the descriptions of assembly and use already given. The differences are simply that in this embodiment the interactions between the Guide Tab 2150, the Tab Channel 2336, and the Pin 2120 discussed above take the place of the interaction between the Pins 1120 and the Pin Receiving Slots 146.

While a number of embodiments of the present invention have been described, it is understood that these embodiments are illustrative only, and not restrictive, and that many modifications may become apparent to those of ordinary skill in the art. For example, the present invention may be placed at any desired level of the spine. Further, the present invention may be used in conjunction with a posterior spinal rod implantation. Further still, the controllable angulation provided by the present invention may be in any desired number of planes. Further still, the rod may be fixed axially and rotationally. Further still, any element described herein may be provided in any desired size (e.g., any element described herein may be provided in any desired custom size or any element described herein may be provided in any desired size selected from a "family" of sizes, such as small, medium, large). To give a more specific example (which example is intended to be illustrative and not restrictive), a bone screw may be provided in a desired thread pitch, thread outer diameter, shaft outer diameter, shaft outer diameter to thread outer diameter ratio and/or length and a body element may be provided in any desired inner diameter, outer diameter, lateral offset, angle and/or length. Further still, the compression element may have a "break-off" feature for separating from the installed portion of the compression element when a desired amount of torque has been applied.

Further still, one or more of the components of the fastener assembly may be made from any of the following materials: (a) any biocompatible material (which biocompatible material may be treated to permit bone ingrowth or prohibit bone ingrowth—depending upon the desire of the surgeon); (b) a plastic; (c) a fiber; (d) a polymer; (e) a metal (a pure metal such as titanium and/or an alloy such as Ti—Al—Nb, Ti-6Al-4V, stainless steel); (f) any combination thereof.

Further still, use of the guide wire for guiding the fastener via the cannulation may be useful during a minimally invasive procedure, for example. Further still, the bone screw may be adapted for placement in cancellous bone. Further still, rather than a thread, the fastener may employ a hook for attachment to bone.

Further still, an outer surface of the head of the fastener, an outer surface of the rod, an outer surface of the retention ring, an inner surface of the retention ring and/or an inner surface of the body (e.g., at any interface area between the aforementioned components) may have one or more features for increasing friction at the interface. For example, any of the aforementioned components may have: a roughened or treated surface (e.g., via sandblasting or knurling), a threaded surface, a grooved surface, a ridged surface, a surface with protrusions, and/or a surface with indentations. Further still, a minimum of two fastener assemblies for each rod may be used (e.g., for stabilization purposes). Further still, any type and number of features may be utilized for interfacing with an installation tool (see, e.g., the holes disposed on the outer surface of the body of the device—these holes may mate with corresponding retractable pins of an installation tool). Further still, any steps described herein may be carried out in any desired order (and any additional desired steps may be added and/or any desired steps deleted).

What is claimed is:

1. A fixation system, comprising:
a body, wherein the body has a first end and a second end;
a body rod receiving channel disposed adjacent the first end of the body and defined by a first wall and a second wall of the body;
a fastener head receiving chamber disposed adjacent the second end of the body, wherein the fastener head receiving chamber is tapered towards the second end of the body, and wherein the body rod receiving channel and the fastener head receiving chamber are operatively connected;
a pin mounting channel positioned in the body having a first diameter that is larger than a second diameter;

a pin fixably attached to the body via the pin mounting channel, wherein the pin includes a pin head that is larger than a pin shaft, the pin head is configured to not extend beyond the first diameter of the pin mounting channel;

a pressure cap slidably engaged with a body engagement element, wherein the pressure cap includes pin receiving slots that extend through an entire width of a wall of the pressure cap, and wherein the pin receiving slots are elongated so that the pressure cap slidably moves within the body's first and second ends; and a compression element configured to cooperate with the body that urges a rod, when the rod is disposed within the body rod receiving channel, into contact with at least part of the pressure cap.

2. The fixation system of claim 1, further comprising a fastener having a head at a first end, wherein the head of the fastener includes a drive element, wherein the pressure cap is configured to press the head of the fastener towards the tapered end of the fastener head receiving chamber.

3. The fixation system of claim 1, further comprising a retention device disposed within the fastener head receiving chamber and configured to retain a fastener head within the fastener head receiving chamber.

4. The fixation system of claim 3, wherein the retention device is a split ring.

5. The fixation system of claim 1, further comprising a flange disposed over a body aperture at the second end of the body, wherein the flange has an elongated flange aperture.

6. The fixation system of claim 5, wherein the flange is integral to the body.

7. The fixation system of claim 1, wherein the pressure cap comprises:
    a fastener head receiving face configured to contact a fastener head; and
    a pressure cap rod receiving channel, wherein the pin receiving slots are configured to slideably engage with the pin.

8. The fixation system of claim 7, wherein at least one of the pin receiving slots include a tab that is disposed within a tab channel of the body.

9. The fixation system of claim 1, further comprising a rib configured to bridge a top portion of the first and second walls of the body rod receiving channel and thereby prevents a rod that is positioned in the body rod receiving channel to be moved passed the top portions of the first and second walls.

10. The fixation system of claim 9, wherein the body comprises an aperture in one of the walls of the body rod receiving channel.

11. The fixation system of claim 1, wherein the body rod receiving channel comprises an extension of a wall of the body rod receiving channel removeably connected to the body at the first end.

12. The fixation system of claim 1, wherein the compression element is a set screw.

* * * * *